United States Patent
Bao et al.

(10) Patent No.: US 11,760,703 B2
(45) Date of Patent: *Sep. 19, 2023

(54) PROCESSES FOR UPGRADING ALKANES AND ALKYL AROMATIC HYDROCARBONS

(71) Applicant: ExxonMobil Chemical Patents Inc., Baytown, TX (US)

(72) Inventors: Xiaoying Bao, Houston, TX (US); John S. Coleman, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/744,890

(22) Filed: May 16, 2022

(65) Prior Publication Data

US 2022/0274901 A1  Sep. 1, 2022

Related U.S. Application Data

(63) Continuation-in-part of application No. 17/174,078, filed on Feb. 11, 2021.
(Continued)

(30) Foreign Application Priority Data

Jun. 11, 2020  (EP) ..................................... 20179409

(51) Int. Cl.
  *C07C 5/333*  (2006.01)
  *B01J 21/10*  (2006.01)
  (Continued)

(52) U.S. Cl.
  CPC ............. *C07C 5/3337* (2013.01); *B01J 21/04* (2013.01); *B01J 21/066* (2013.01); *B01J 21/10* (2013.01);
  (Continued)

(58) Field of Classification Search
  None
  See application file for complete search history.

(56) References Cited

U.S. PATENT DOCUMENTS

| 3,888,762 A | 6/1975 | Gerhold | 208/120 |
| 4,502,947 A | 3/1985 | Haddad et al. | 208/161 |
| (Continued) | | | |

FOREIGN PATENT DOCUMENTS

| EP | 0098622 | 3/1986 | B01J 23/62 |
| EP | 1016641 | 7/2000 | B01J 23/00 |
| (Continued) | | | |

OTHER PUBLICATIONS

Sande et al. "Fine Mesh Computational Fluid Dynamics Study on Gas-Fluidization of Geldart A Particles: Homogeneous to Bubbling Bed" I&EC Research 2016, 22, 2623-2633 (Year: 2016).*
(Continued)

*Primary Examiner* — In Suk C Bullock
*Assistant Examiner* — Alyssa L Cepluch

(57) ABSTRACT

Processes for upgrading a hydrocarbon. The process can include contacting a hydrocarbon-containing feed with fluidized catalyst particles that can include a Group 8-10 element or a compound thereof disposed on a support to effect one or more of dehydrogenation, dehydroaromatization, and dehydrocyclization of at least a portion of the hydrocarbon-containing feed to produce coked catalyst particles and an effluent. The process can also include contacting at least a portion of the coked catalyst particles with an oxidant to effect combustion of at least a portion of the coke to produce regenerated catalyst particles. The process can also include contacting at least a portion of the regenerated catalyst particles with a reducing gas to produce regenerated and reduced catalyst particles. The process can also include contacting an additional quantity of the hydrocarbon-containing feed with fluidized regenerated and reduced catalyst (Continued)

particles to produce additional effluent and re-coked catalyst particles.

25 Claims, 9 Drawing Sheets

Related U.S. Application Data

(60) Provisional application No. 62/993,985, filed on Mar. 24, 2020, provisional application No. 62/986,229, filed on Mar. 6, 2020.

(51) Int. Cl.
| | |
|---|---|
| C07C 5/41 | (2006.01) |
| B01J 38/10 | (2006.01) |
| B01J 21/04 | (2006.01) |
| B01J 21/06 | (2006.01) |
| B01J 35/00 | (2006.01) |
| B01J 23/62 | (2006.01) |
| B01J 23/10 | (2006.01) |

(52) U.S. Cl.
CPC .......... *B01J 23/10* (2013.01); *B01J 23/626* (2013.01); *B01J 35/0026* (2013.01); *B01J 38/10* (2013.01); *C07C 5/417* (2013.01); *C07C 2521/04* (2013.01); *C07C 2521/06* (2013.01); *C07C 2521/10* (2013.01); *C07C 2523/10* (2013.01); *C07C 2523/62* (2013.01)

(56) References Cited

U.S. PATENT DOCUMENTS

| | | | | |
|---|---|---|---|---|
| 4,788,371 | A | 11/1988 | Imai et al. | 585/443 |
| 4,806,624 | A * | 2/1989 | Herber | C07C 5/325 |
| | | | | 585/440 |
| 4,962,265 | A | 10/1990 | De Clippeleir et al. | 585/660 |
| 4,985,136 | A | 1/1991 | Bartholic | 208/153 |
| 5,248,411 | A | 9/1993 | Chan | 208/161 |
| 5,633,421 | A | 5/1997 | Iezzi et al. | 585/660 |
| 5,817,596 | A | 10/1998 | Akporiaye et al. | 502/327 |
| 5,922,925 | A | 7/1999 | Akporiaye et al. | 585/660 |
| 6,313,063 | B1 | 11/2001 | Rytter et al. | 502/327 |
| 6,582,589 | B2 | 6/2003 | Rytter et al. | 208/134 |
| 6,967,182 | B1 | 11/2005 | Olsbye et al. | 502/84 |
| 7,102,050 | B1 | 9/2006 | Lattner et al. | 585/640 |
| 7,122,160 | B2 | 10/2006 | Brookhart | 422/145 |
| 7,195,741 | B2 | 3/2007 | Lattner et al. | 422/141 |
| 8,653,317 | B2 * | 2/2014 | Pierce | C07C 5/3337 |
| | | | | 585/440 |
| 10,227,271 | B2 | 3/2019 | Pretz | C07C 5/3332 |
| 2002/0098976 | A1 * | 7/2002 | Rytter | C07C 5/3337 |
| | | | | 502/340 |
| 2003/0139637 | A1 | 7/2003 | Rytter et al. | 585/658 |
| 2004/0029729 | A1 | 2/2004 | Rytter et al. | 502/341 |
| 2004/0082824 | A1 | 4/2004 | Lattner | 585/638 |
| 2005/0003960 | A1 | 1/2005 | Rytter et al. | 502/335 |
| 2008/0194891 | A1 | 8/2008 | Pretz et al. | 585/252 |
| 2010/0236985 | A1 | 9/2010 | Luo et al. | 208/138 |
| 2013/0253249 | A1 | 9/2013 | Baucherel | 585/661 |
| 2016/0272559 | A1 * | 9/2016 | Pretz | C07C 5/3337 |
| 2020/0038852 | A1 * | 2/2020 | Kimura | B01J 37/0205 |
| 2021/0139796 | A1 | 5/2021 | Agrawal et al. | C10G 59/02 |
| 2021/0276932 | A1 | 9/2021 | Bao | C07C 5/3337 |
| 2022/0282165 | A1 | 9/2022 | Bao | C10G 29/04 |

FOREIGN PATENT DOCUMENTS

| | | | |
|---|---|---|---|
| WO | WO1999/046039 | 9/1999 | B01J 21/10 |
| WO | WO2001/085872 | 11/2001 | C10G 11/18 |
| WO | WO2004/029178 | 4/2004 | C10G 3/00 |
| WO | WO2005/077867 | 8/2005 | C07C 5/00 |
| WO | WO2018/193668 | 10/2018 | C07C 5/333 |
| WO | WO-2018193668 A1 * | 10/2018 | B01J 23/62 |
| WO | WO2020/046978 | 3/2020 | C07C 5/48 |

OTHER PUBLICATIONS

Reichle, W. T. (1985) "Catalytic Reactions by Thermally Activated, Synthetic, Anionic Clay Minerals," *Jrnl. of Catalysis*, v. 94(2), pp. 547-557.
Sande, P. et al. (2016) "Fine Mesh Computational Fluid Dynamics Study on Gas-Fluidization of Geldart A Particles: Homogeneous to Bubbling Bed," *I&EC Research*, v.22, pp. 2623-2633.
Schaper, H. et al. (1989) "Stabilized Magnesia: A Novel Catalyst (support) Material," *Applied Catalysis*, v. 54(1), pp. 79-90.
Teleki, A. et al. (2008) "Distinguishing Between Aggregates and Agglomerates of Flame-Made $TiO_2$ by High-Pressure Dispersion," *Powder Tech.*, v.181(3), pp. 292-300.

* cited by examiner

PROCESSES FOR UPGRADING ALKANES AND ALKYL AROMATIC HYDROCARBONS

CROSS-REFERENCE OF RELATED APPLICATIONS

This application is a continuation-in-part of U.S. patent application Ser. No. 17/174,078, filed on Feb. 11, 2021, which claims priority to and the benefit of U.S. Provisional Application Nos. 62/993,985, filed on Mar. 24, 2020, and 62/986,229, filed on Mar. 6, 2020, and EP Application No. 20179409.6, filed on Jun. 11, 2020, the disclosures of which are all incorporated herein by reference in their entirety.

FIELD

This disclosure relates to processes for upgrading alkanes and/or alkyl aromatic hydrocarbons. More particularly, this disclosure relates to processes for dehydrogenating, dehydroaromatizing, and/or dehydrocyclizing one or more alkanes and/or one or more alkyl aromatic hydrocarbons in the presence of fluidized catalyst particles to produce an effluent that includes one or more upgraded hydrocarbons.

BACKGROUND

Catalytic dehydrogenation, dehydroaromatization, and dehydrocyclization of alkanes and/or alkyl aromatic hydrocarbons are industrially important chemical conversion processes that are endothermic and equilibrium-limited. The dehydrogenation of alkanes, e.g., $C_2$-$C_{16}$ alkanes, and/or alkyl aromatic hydrocarbons, e.g., ethylbenzene, can be done through a variety of different supported catalyst particle systems such as the Pt-based, Cr-based, Ga-based, V-based, Zr-based, In-based, W-based, Mo-based, Zn-based, and Fe-based systems. Among the existing propane dehydrogenation processes, a certain process uses an alumina supported chromia catalyst that provides one of the highest propylene yields at approximately 50% (55% propane conversion at 90% propylene selectivity), which is obtained at a temperature of approximately 560° C. to 650° C. and at a low pressure of 20 kPa-absolute to 50 kPa-absolute. It is desirable to increase the propylene yield without having to operate at such low pressure to increase the efficiency of the dehydrogenation process.

Increasing the temperature of the dehydrogenation process is one way to increase the conversion of the process according to the thermodynamics of the process. For example, at 670° C., 100 kPa-absolute, in the absence of any inert/diluent, the equilibrium propylene yield has been estimated via simulation to be approximately 74%. At such high temperature, however, the catalyst particles deactivate very rapidly and/or the propylene selectivity becomes uneconomically low. The rapid deactivation of the catalyst particles is believed to be caused by coke depositing onto the catalyst particles and/or agglomeration of the active phase. Coke can be removed by combustion using an oxygen-containing gas, however, agglomeration of the active phase is believed to be exacerbated during the combustion process, which rapidly reduces the activity and stability of the catalyst particles.

There is a need, therefore, for improved processes and catalyst particles for dehydrogenating, dehydroaromatizing, and/or dehydrocyclizing alkanes and/or alkyl aromatic hydrocarbons. This disclosure satisfies this and other needs.

SUMMARY

Processes for upgrading alkanes and/or alkyl aromatic hydrocarbons are provided. In some embodiments, the process for upgrading a hydrocarbon can include (I) contacting a hydrocarbon-containing feed with fluidized catalyst particles that can include a Group 8-10 element disposed on a support within a conversion zone to effect one or more of dehydrogenation, dehydroaromatization, and dehydrocyclization of at least a portion of the hydrocarbon-containing feed to produce a conversion effluent that can include coked catalyst particles, one or more upgraded hydrocarbons, and molecular hydrogen. The hydrocarbon-containing feed can include one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof. The hydrocarbon-containing feed and catalyst particles can be contacted at a temperature in a range from 300° C. to 900° C., for a time period in a range from 0.1 seconds to 2 minutes, and under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the hydrocarbon-containing feed. The catalyst particles can include from 0.001 wt % to 6 wt % of the Group 8-10 element based on the weight of the support. The one or more upgraded hydrocarbons can include a dehydrogenated hydrocarbon, a dehydroaromatized hydrocarbon, a dehydrocylized hydrocarbon, or a mixture thereof. The process can also include (II) obtaining from the conversion effluent a first gaseous stream rich in the one or more upgraded hydrocarbons and the molecular hydrogen and a first particle stream rich in the coked catalyst particles. The process can also include (III) contacting at least a portion of the coked catalyst particles in the first particle stream with an oxidant in a combustion zone to effect combustion of at least a portion of the coke to produce a combustion effluent that can include regenerated catalyst particles lean in coke and a combustion gas. The process can also include (IV) obtaining from the combustion effluent a second gaseous stream rich in the combustion gas and a second particle stream rich in the regenerated catalyst particles. The process can also include (IVa) contacting at least a portion of the regenerated catalyst particles with a reducing gas for a time period in a range from 1 second to less than 30 minutes to produce regenerated and reduced catalyst particles. The process can also include (V) contacting an additional quantity of the hydrocarbon-containing feed with fluidized regenerated and reduced catalyst particles to produce additional conversion effluent comprising re-coked catalyst particles, additional one or more upgraded hydrocarbons, and additional molecular hydrogen. A cycle time from the contacting the hydrocarbon-containing feed with the catalyst particles in step (I) to the contacting the additional quantity of the hydrocarbon-containing feed with the fluidized regenerated and reduced catalyst particles in step (V) can be ≤60 minutes.

DETAILED DESCRIPTION

Figure 1:
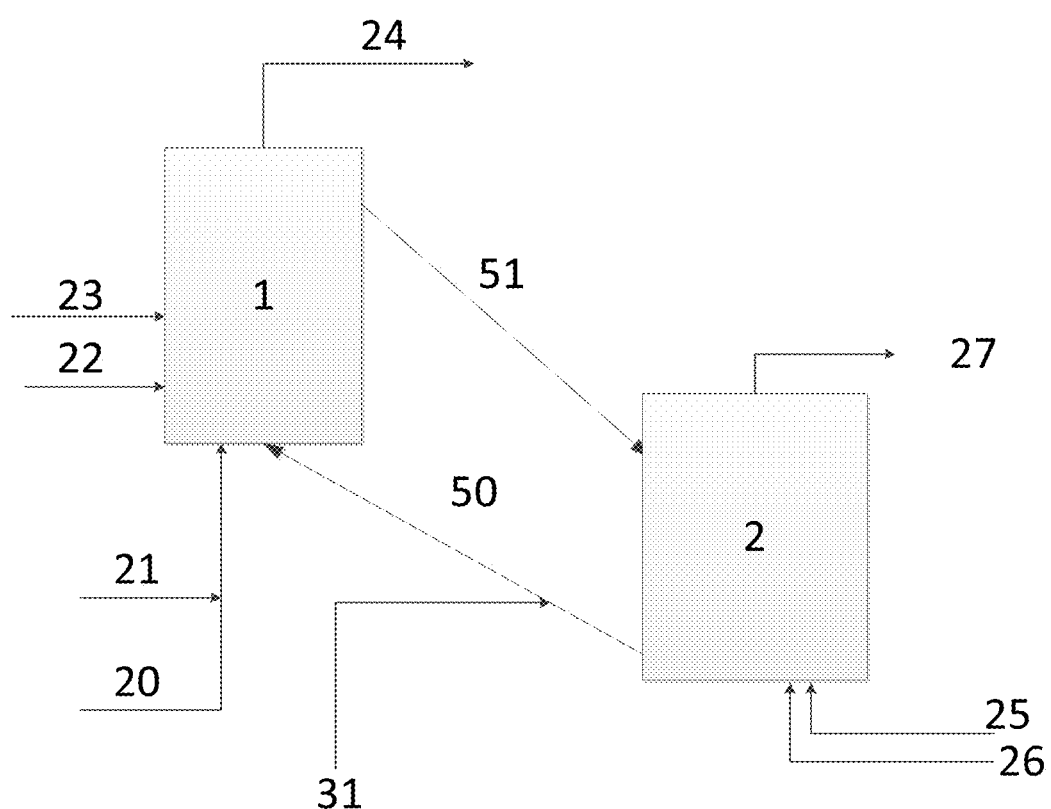
FIG. 1 depicts a system for upgrading a hydrocarbon-containing feed that includes a reactor and a regenerator, according to one or more embodiments described.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

The indefinite article "a" or "an", as used herein, means "at least one" unless specified to the contrary or the context clearly indicates otherwise. Thus, embodiments using "a reactor" or "a conversion zone" include embodiments where one, two or more reactors or conversion zones are used, unless specified to the contrary or the context clearly indicates that only one reactor or conversion zone is used.

The terms "up" and "down"; "upward" and "downward"; "upper" and "lower"; "upwardly" and "downwardly"; "above" and "below"; and other like terms used herein refer to relative positions to one another and are not intended to denote a particular spatial orientation since the apparatus and methods of using the same may be equally effective at various angles or orientations.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion.

A "Cn+ hydrocarbon" means (i) any hydrocarbon compound comprising carbon atom(s) in its molecule at the total number of at least n, or (ii) any mixture of two or more such hydrocarbon compounds in (i). A "Cn-hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

For the purposes of this disclosure, the nomenclature of elements is pursuant to the version of the Periodic Table of Elements (under the new notation) as provided in Hawley's Condensed Chemical Dictionary, 16$^{th}$ Ed., John Wiley & Sons, Inc., (2016), Appendix V. For example, a Group 8 element can include one or more of Fe, Ru, and Os, a Group 9 element can include one or more of Co, Rh, and Ir, and a group 10 element can include one or more of Ni, Pd, and Pt. The term "metalloid", as used herein, refers to the following elements: B, Si, Ge, As, Sb, Te, and At. In this disclosure, when a given element is indicated as present, it can be present in the elemental state or as any chemical compound thereof, unless it is specified otherwise or clearly indicated otherwise by the context.

The term "alkane" means a saturated hydrocarbon. The term "cyclic alkane" means a saturated hydrocarbon comprising a cyclic carbon ring in the molecular structure thereof. An alkane can be linear, branched, or cyclic.

The term "aromatic" is to be understood in accordance with its art-recognized scope, which includes alkyl substituted and unsubstituted mono- and polynuclear compounds.

The term "rich" when used in phrases such as "X-rich" or "rich in X" means, with respect to an outgoing stream obtained from a device, e.g., a conversion zone, that the stream comprises material X at a concentration higher than in the feed material fed to the same device from which the stream is derived. The term "lean" when used in phrases such as "X-lean" or "lean in X" means, with respect to an outgoing stream obtained from a device, e.g., a conversion zone, that the stream comprises material X at a concentration lower than in the feed material fed to the same device from which the stream is derived.

The term "mixed metal oxide" refers to a composition that includes oxygen atoms and at least two different metal atoms that are mixed on an atomic scale. For example, a "mixed Mg/Al metal oxide" has O, Mg, and Al atoms mixed on an atomic scale and is substantially the same as or identical to a composition obtained by calcining an Mg/Al hydrotalcite that has the general chemical formula $[Mg_{(1-x)}Al_x(OH)_2](A_{x/n}{}^{n-})\cdot mH_2O$, where A is a counter anion of a negative charge n, x is in a range of from >0 to <1, and m is ≥0. A material consisting of nm sized MgO particles and nm sized $Al_2O_3$ particles mixed together is not a mixed metal oxide because the Mg and Al atoms are not mixed on an atomic scale but are instead mixed on a nm scale.

The term "selectivity" refers to the production (on a carbon mole basis) of a specified compound in a catalytic reaction. As an example, the phrase "an alkane hydrocarbon conversion reaction has a 100% selectivity for an olefin hydrocarbon" means that 100% of the alkane hydrocarbon (carbon mole basis) that is converted in the reaction is converted to the olefin hydrocarbon. When used in connection with a specified reactant, the term "conversion" means the amount of the reactant consumed in the reaction. For example, when the specified reactant is propane, 100% conversion means 100% of the propane is consumed in the reaction. In another example, when the specified reactant is propane, if one mole of propane converts to one mole of methane and one mole of ethylene, the selectivity to methane is 33.3% and the selectivity to ethylene is 66.7%. Yield (carbon mole basis) is conversion times selectivity.

Overview

The hydrocarbon-containing feed can be or can include, but is not limited to, one or more alkanes, e.g., $C_2$-$C_{16}$ linear or branched alkanes and/or $C_4$-$C_{16}$ cyclic alkanes, and/or one or more alkyl aromatic hydrocarbons, e.g., $C_8$-$C_{16}$ alkyl aromatic hydrocarbons. In some embodiments, the hydrocarbon-containing feed can optionally include 0.1 vol % to 50 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include <0.1 vol % of steam or can be free of steam, based on the total volume of any $C_2$-$C_{16}$ alkanes and any $C_8$-$C_{16}$ alkyl aromatic hydrocarbons in the hydrocarbon-containing feed. The hydrocarbon-containing feed can be contacted with fluidized catalyst particles in a conversion zone that include one or more Group 8-10 elements, e.g., Pt, disposed on a support to effect one or more of dehydrogenation, dehydroaromatization, and dehydrocyclization of at least a portion of the hydrocarbon-containing feed to produce a conversion effluent that can include coked catalyst particles and an effluent that can include one or more upgraded hydrocarbons and molecular hydrogen. The one or more upgraded hydrocarbons can be or can include one or more dehydrogenated hydrocarbons, one or more dehydroaromatized hydrocarbons, one or more dehydrocyclized hydrocarbons, or a mixture thereof. The hydrocarbon-containing feed and catalyst particles can be contacted at a temperature in a range from 300° C. to 900° C. for a time period in a range from 0.1 seconds to 2 or even 3 minutes, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the hydrocarbon-containing feed. The catalyst particles can include from 0.001 wt % to 6 wt % of the Group 8-10 element, e.g., Pt, based on the weight of the support. The support can be or can include, but is not limited to, a Group 2 element, a Group 4 element, a Group 12 element, an element having an atomic number of 21, 39, or 57-71, or a compound thereof.

A first gaseous stream rich in the one or more upgraded hydrocarbons and molecular hydrogen and a first particle stream rich in the coked catalyst particles can be separated or otherwise obtained from the conversion effluent. At least a portion of the coked catalyst particles in the first particle stream can be contacted with one or more oxidants in a conversion zone to effect combustion of at least a portion of the coke to produce a combustion effluent that can include regenerated catalyst particles lean in coke and a combustion gas. A second gaseous stream rich in the combustion gas and a second particle stream rich in the regenerated catalyst particles can be separated or otherwise obtained from the combustion effluent. An additional quantity of the hydrocarbon-containing feed can be contacted with the fluidized regenerated catalyst particles to produce re-coked catalyst particles and additional conversion effluent that includes re-coked catalyst particles, additional one or more upgraded hydrocarbons, and additional molecular hydrogen. In some embodiments, a cycle time from contacting the hydrocarbon-containing feed with the catalyst particles to contacting the additional quantity of the hydrocarbon-containing feed with the regenerated catalyst particles can be ≤70 minutes, e.g., from 1 minute, 5 minutes, 10 minutes, or 20 minutes to 30 minutes 45 minutes, 60 minutes, or 70 minutes.

The catalyst particles disclosed herein may exhibit improved activity and selectivity after undergoing an additional reduction step prior to recontact with the hydrocarbon-containing feed. Additionally, the post-reduced catalyst particles may maintain the improved activity and selectivity for 10 minutes or more in the presence of the hydrocarbon-containing feed. Accordingly, in some embodiments the process can optionally include contacting at least a portion of the regenerated catalyst particles in the second particle stream with a reducing gas to produce regenerated and reduced catalyst particles. In this embodiment, the additional quantity of the hydrocarbon-containing feed can be contacted with at least a portion of the regenerated and reduced catalyst particles to produce the additional conversion effluent. In other embodiments the process can include contacting at least a portion of the regenerated catalyst particles and at least a portion of the regenerated and reduced catalyst particles with the additional quantity of the hydrocarbon-containing feed to produce the additional conversion effluent. In still other embodiments, the process can include contacting at least a portion of the regenerated catalyst particles, at least a portion of the regenerated and reduced catalyst particles, and/or new or make-up catalyst particles to produce the additional conversion effluent. If the process includes the optional reduction step, the cycle time from contacting the hydrocarbon-containing feed with the catalyst particles to contacting the additional quantity of the hydrocarbon-containing feed with the regenerated and reduced catalyst particles can also be ≤70 minutes, e.g., from 1 minute, 5 minutes, 10 minutes, or 20 minutes to 25 minutes, 30 minutes, 35 minutes, 40 minutes, 45 minutes, 50 minutes, 55 minutes, 60 minutes, or 70 minutes. In some embodiments, the cycle time from contacting the hydrocarbon-containing feed with the catalyst particles to contacting the additional quantity of the hydrocarbon-containing feed with the regenerated and reduced catalyst particles can be ≤60 minutes, ≤55 minutes, ≤50 minutes, or ≤45 minutes.

It has been surprisingly and unexpectedly discovered that the catalyst particles that include the Group 8-10 element, e.g., Pt, disposed on the support can remain sufficiently active and stable after many cycles, e.g., at least 15, at least 20, at least 30, at least 40, at least 50, at least 60, at least 70, at least 100 cycles, at least 125 cycles, at least 150 cycles, at least 175 cycles, or at least 200 cycles with each cycle time lasting for ≤70 minutes. In some embodiments, after the performance of the catalyst particles stabilizes (sometimes the few first cycle can have a relatively poor or relatively good performance, but the performance can eventually stabilize), the process can produce a first upgraded hydrocarbon product yield, e.g., propylene when the hydrocarbon-containing feed includes propane, at an upgraded hydrocarbon selectivity, e.g., propylene, of ≥75%, ≥80%, ≥85%, or ≥90%, or ≥95% when initially contacted with the hydrocarbon-containing feed, and can have a second upgraded hydrocarbon product yield upon completion of the last cycle (at least 15 cycles total) that can be at least 90%, at least 93%, at least 95%, at least 97%, at least 98%, at least 99%, at least 99.5%, or at least 100% of the first upgraded hydrocarbon product yield at an upgraded hydrocarbon selectivity, e.g., propylene, of ≥75%, ≥80%, ≥85%, or ≥90%, or ≥95%. Prior to this discovery, it was believed that catalyst particles having a Group 8-10 element, e.g., Pt, as the active component would not maintain sufficient activity and stability when subjected to so many short cycles with a simple oxidative regeneration that requires no addition of halogen.

The first cycle begins upon contact of the catalyst particles with the hydrocarbon-containing feed, followed by contact with at least the oxidant to produce the regenerated catalyst particles or at least the oxidant and the optional reducing gas to produce the regenerated and reduced catalyst particles, and the first cycle ends upon contact of the regenerated catalyst particles or the regenerated and reduced catalyst particles with the additional quantity of the hydrocarbon-containing feed. The second and each subsequent cycle begins upon contact of the regenerated catalyst particles or the regenerated and reduced catalyst particles and the additional quantity of the hydrocarbon-containing feed and the second and each subsequent cycle ends upon contact of additional or subsequently regenerated catalyst particles or regenerated and reduced catalyst particles with the additional quantity of the hydrocarbon-containing feed.

Furthermore, unprecedented propylene yields have been obtained via the processes and catalyst particles described herein. In some embodiments, when the hydrocarbon-containing feed includes propane and the upgraded hydrocarbon includes propylene, contacting the hydrocarbon-containing feed with the catalyst particles can produce a propylene yield of at least 48%, at least 49%, at least 50%, at least 51%, at least 52%, at least 53%, at least 55%, at least 57%, at least 60%, at least 62%, at least 63%, at least 64%, at least 65%, at least 66%, at least 67%, at least 68%, or at least 69% at a propylene selectivity of at least 75%, at least 80%, at least 85%, at least 90%, or at least 95% for at least 15, at least 20, at least 30, at least 40, at least 50, at least 60, at least 70, at least 100 cycles, at least 125 cycles, at least 150 cycles, at least 175 cycles, or at least 200 cycles. In other embodiments, when a hydrocarbon-containing feed includes at least 70 vol % of propane, based on a total volume of the hydrocarbon-containing feed, is contacted under a propane partial pressure of at least 20 kPa-absolute, a propylene yield of at least 48%, at least 49%, at least 50%, at least 51%, at least 52%, at least 53%, at least 55%, at least 57%, at least 60%, at least 62%, at least 63%, at least 64%, at least 65%, at least 66%, at least 67%, at least 68%, or at least 69% at a propylene selectivity of at least 75%, at least 80%, at least 85%, at least 90%, or at least 95% can be obtained for at least 15, at least 20, at least 30, at least 40, at least 50, at least 60, at least 70, at least 100 cycles, at least 125 cycles, at least 150 cycles, at least 175 cycles, or at least 200 cycles. It is believed that the propylene yield can be further increased to at least 70%, at least 72%, at least 75%, at least 77%, at least 80%, or at least 82% at a propylene selectivity of at least 75%, at least 80%, at least 85%, at least 90%, or at least 95% for at least 15 cycles, at least 20, at least 30, at least 40, at least 50, at least 60, at least 70, at least 100 cycles, at least 125 cycles, at least 150 cycles, at least 175 cycles, or at least 200 cycles by further optimizing the composition of the support and/or adjusting one or more process conditions. In some embodiments, the propylene yield can be obtained when the catalyst particles is contacted with the hydrocarbon-containing feed at a temperature of at least 620° C., at least 630° C., at least 640° C., at least 650° C., at least 655° C., at least 660° C., at least 670° C., at least 680° C., at least 690° C., at least 700° C., or at least 750° C. for at least 15, at least 20, at least 30, at least 40, at least 50, at least 60, at least 70, at least 100 cycles, at least 125 cycles, at least 150 cycles, at least 175 cycles, or at least 200 cycles. Such a high propylene yield under such processing conditions was not thought possible.

Hydrocarbon Upgrading Process

The hydrocarbon-containing feed can be contacted with the catalyst particles within any suitable conversion zone to effect one or more of dehydrogenation, dehydroaromatization, and dehydrocyclization of at least a portion of the hydrocarbon-containing feed to produce the conversion effluent that can include the coked catalyst particles, the one or more upgraded hydrocarbons, and the molecular hydrogen. In some embodiments, the hydrocarbon-containing feed and the catalyst particles can be contacted in a conversion zone disposed within a continuous type process commonly employed in fluidized bed reactors. In some embodiments, the conversion zone can be disposed within a riser reactor. In other embodiments, the conversion zone can be disposed within a downer reactor. In still other embodiments, the conversion zone can be disposed within a vortex reactor. In other embodiments, the conversion zone can be disposed within a reactor and can allow the fluidized particles to form a relatively dense turbulent fluidized bed therein during contact with the hydrocarbon-containing feed. A relatively dense turbulent fluidized bed refers to a fluidized bed that is at a superficial gas velocity above the transition velocity designated as the critical velocity between the transition of a bubbling and turbulent bed, but below the transport velocity that demarcates a fast fluidization regime in which the catalyst particles are conveyed such as in a riser reactor.

Any number of reactors can be operated in series and/or in parallel. Any two or more types of reactors can be used in combination with one another. If two or more reactors are used the reactors can be operated at the same conditions and/or different conditions and can receive the same hydrocarbon-containing feed or different hydrocarbon-containing feeds. If two or more reactors are used the reactors can be arranged in series, in parallel, or a combination thereof with respect to one another. In some embodiments, suitable reactors can be or can include, but are not limited to, high gas velocity riser reactors, high gas velocity downer reactors, vortex reactors, reactors having a relatively dense fluidized catalyst bed at a first or bottom end and a relatively less dense fluidized catalyst within a riser located at a second or top end, multiple riser reactors and/or downer reactors operated in parallel and/or series operating at the same or different conditions with respect to one another, or combinations thereof.

In some examples, the catalyst particles can be pneumatically moved through the reaction system, e.g., fed into the conversion zone, fed into the combustion zone, transported through conduits connecting two or more locations, and the like, via a carrier fluid or transport fluid. The transport fluid can be or can include, but is not limited to, a diluent, one or more of the reactants in gaseous form, i.e., the one or more $C_2$-$C_{16}$ alkanes, the one or more $C_8$-$C_{16}$ alkyl aromatic hydrocarbons, or a mixture thereof. Suitable transport fluids can be or can include, but are not limited to, molecular nitrogen, volatile hydrocarbons such methane, ethane, and/or propane, argon, carbon monoxide, carbon dioxide, steam, and the like. The amount of transport fluid can be sufficient to maintain the catalyst particles in a fluidized state and to transport the catalyst particles from one location, e.g., the combustion zone or the regeneration zone, to a second location, e.g., the conversion zone. In some embodiments, a weight ratio of the catalyst particles to the transport fluid can be in a range from 5, 10, 15, or 20 to 50, 60, 80, 90, or 100. Injection points for the transport fluid, as can be made at multiple points along any one or more transfer lines that connect any two zones or other locations such as the combustion zone and the conversion zone or the regeneration zone and the conversion zone.

The hydrocarbon-containing feed and catalyst particles can be contacted at a temperature in a range from 300° C., 350° C., 400° C., 450° C., 500° C., 550° C., 600° C., 620° C., 630° C., 640° C., 650° C., 660° C., 670° C., 680° C., 690° C., or 700° C. to 725° C., 750° C., 760° C., 780° C., 800° C., 825° C., 850° C., 875° C., or 900° C. In some embodiments, the hydrocarbon-containing feed and catalyst particles can be contacted at a temperature of at least 620° C., at least 630° C., at least 640° C., at least 650° C., at least 660° C., at least 670° C., at least 680° C., at least 690° C., or at least 700° C. to 725° C., 750° C., 760° C., 780° C., 800° C., 825° C., 850° C., 875° C., or 900° C. The hydrocarbon-containing feed can be introduced into the conversion zone and contacted with the catalyst particles therein for a time period in a range from 0.1 seconds, 1 second, 1.5 seconds, 2 seconds, or 3 seconds to 5 seconds, 10 seconds, 20 seconds, 30 seconds, 45 seconds, 1 minute, 1.5 minutes, 2 minutes, 2.5 minutes, or 3 minutes.

The average residence time of the catalyst particles within the conversion zone can be ≤7 minutes, ≤6 minutes, ≤5 minutes, ≤4 minutes ≤3 minutes, ≤2 minutes, ≤1.5 minutes, ≤1 minute, ≤45 seconds, ≤30 seconds, ≤20 seconds, ≤15 seconds, ≤10 seconds, ≤7 seconds, ≤5 seconds, ≤3 seconds, ≤2 seconds, or ≤1 second. In some embodiments, the average residence time of the catalyst particles within the conversion zone can be greater than an average residence time of the gaseous components, e.g., the hydrocarbon-containing feed and the conversion effluent obtained therefrom within the conversion zone.

The hydrocarbon-containing feed and catalyst particles can be contacted under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the hydrocarbon-containing feed. In some embodiments, the hydrocarbon partial pressure during contact of the hydrocarbon-containing feed and the catalyst particles can be in a range from 20 kPa-absolute, 50 kPa-absolute, 70 kPa-absolute, 100 kPa-absolute, 150 kPa-absolute, or 200 kPa-absolute to 300 kPa-absolute, 500 kPa-absolute, 750 kPa-absolute, or 1,000 kPa-absolute, where the hydrocarbon partial pressure is the total partial pressure of any $C_2$-$C_{16}$ alkanes and any $C_8$-$C_{16}$ alkyl aromatic hydrocarbons in the hydrocarbon-containing feed.

In some embodiments, the hydrocarbon-containing feed can include at least 60 vol %, at least 65 vol %, at least 70 vol %, at least 75 vol %, at least 80 vol %, at least 85 vol %, at least 90 vol %, at least 95 vol %, or at least 99 vol % of a single $C_2$-$C_{16}$ alkane, e.g., propane, based on a total volume of the hydrocarbon-containing feed. The hydrocarbon-containing feed and catalyst particles can be contacted under a single $C_2$-$C_{16}$ alkane, e.g., propane, pressure of at least 20 kPa-absolute, at least 50 kPa-absolute, at least 70 kPa-absolute, at least 100 kPa-absolute, at least 150 kPa-absolute, or at least 250 kPa-absolute to 300 kPa-absolute, 400 kPa-absolute, 500 kPa-absolute, or 1,000 kPa-absolute.

The hydrocarbon-containing feed can be contacted with the catalyst particles within the conversion zone at any weight hourly space velocity (WHSV) effective for carrying out the upgrading process. In some embodiments, the WHSV can be 0.1 $hr^{-1}$, 0.2 $hr^{-1}$, 0.4 $hr^{-1}$, 0.8 $hr^{-1}$, 2 $hr^{-1}$, 4 $hr^{-1}$, or 8 $hr^{-1}$ to 16 $hr^{-1}$, 32 $hr^{-1}$, 64 $hr^{-1}$, or 100 $hr^{-1}$. In some embodiments, a ratio of the catalyst particles to a combined amount of any $C_2$-$C_{16}$ alkanes and any $C_8$-$C_{16}$ alkyl aromatic hydrocarbons can be in a range from 1, 3, 5, 10, 15, 20, 25, 30, or 40 to 50, 60, 70, 80, 90, 100, 110, 125, or 150 on a weight to weight basis.

In some embodiments, at least a portion of the fluidized catalyst particles within the conversion zone can be removed, fed into a heat input device where the catalyst particles can be heated, and the heated catalyst particles can be fed back into the conversion zone. With the reactions occurring within the conversion zone being endothermic, it can be beneficial to remove a portion of the fluidized catalyst particles therefrom to further increase the temperature after some contact with the hydrocarbon-containing feed. The heat can be indirectly transferred from any suitable heat transfer medium, provided via an electric heater, or any other suitable heater typically used to indirectly heat catalyst particles. In another embodiment, heat can be applied within the conversion zone directly.

The first particle stream rich in the coked catalyst particles and the first gaseous stream rich in the one or more upgraded hydrocarbons and the molecular hydrogen can be separated or otherwise obtained from the conversion effluent via any suitable apparatus. In some embodiments, the first particle stream and the first gaseous stream can be obtained from the conversion effluent via one or more solid-gas impingement separators, e.g., one or more cyclone separators. In some examples, the cyclone separator can be or can include a two staged or "coupled" configuration including both positive and negative pressure configurations. In some embodiments, suitable cyclone separators can include those disclosed in U.S. Pat. Nos. 4,502,947; 4,985,136; and 5,248,411. In other embodiments, the first particle stream and the first gaseous stream can be obtained from the conversion effluent via a "T" shaped conduit that can cause the catalyst particles to flow in one direction via gravity and the gaseous components to flow in the other direction.

At least a portion of the coked catalyst particles in the first particle stream can be contacted with the oxidant within a regeneration or combustion zone to produce regenerated catalyst particles. The oxidant can be or can include, but is not limited to, molecular oxygen, ozone, carbon dioxide, steam, or a mixture thereof. In some embodiments, an amount of oxidant in excess of that needed to combust 100% of the coke on the coked catalyst particles can be used to increase the rate of coke removal from the catalyst particles, so that the time needed for coke removal can be reduced and lead to an increased yield in the upgraded product produced within a given period of time. In some embodiments, in addition to the coked catalyst particles, one or more supplemental fuels can also be contacted with the oxidant in the combustion zone to effect combustion of at least a portion of the supplemental fuel to produce heat and additional combustion gas. The optional supplemental fuel can be or can include, but is not limited to, molecular hydrogen, methane, ethane, propane, or a mixture thereof. The optional supplemental fuel can be mixed with an inert gas such as argon, neon, helium, molecular nitrogen, methane, or a mixture thereof.

The coked catalyst particles and oxidant can be contacted with one another at a temperature in a range from 500° C., 550° C., 600° C., 650° C., 700° C., 750° C., or 800° C. to 900° C., 950° C., 1,000° C., 1,050° C., or 1,100° C. to produce the regenerated catalyst particles. In some embodiments, the coked catalyst particles and oxidant can be contacted with one another at a temperature in a range from 500° C. to 1,100° C., 600° C. to 1,100° C., 600° C. to 1,000° C., 650° C. to 950° C., 700° C. to 900° C., or 750° C. to 850° C. to produce the regenerated catalyst particles. The coked catalyst particles and oxidant can be contacted with one another under an oxidant partial pressure in a range from 20 kPa-absolute, 50 kPa-absolute, 70 kPa-absolute, 100 kPa-absolute, 150 kPa-absolute, or 200 kPa-absolute to 300 kPa-absolute, 500 kPa-absolute, 750 kPa-absolute, or 1,000 kPa-absolute.

The coked catalyst particles and oxidant can be contacted with one another for a time period in a range from 15 seconds, 30 seconds, 1 minute, 2 minutes, or 5 minutes to 10 minutes, 20 minutes, 30 minutes, 40 minutes, 50 minutes, or 60 minutes. For example, the coked catalyst particles and oxidant can be contacted with one another for a time period in a range from 2 seconds to 50 minutes, 55 minutes, or 60 minutes. In some embodiments, the coked catalyst particles and oxidant can be contacted for a time period sufficient to remove ≥50 wt %, ≥75 wt %, or ≥90 wt % or >99% of any coke disposed on the catalyst particles.

In some embodiments, the time period the coked catalyst particles and oxidant contact one another can be greater than the time period the catalyst particles contact the hydrocarbon-containing feed to produce the conversion effluent. For example, the time period the coked catalyst particles and oxidant contact one another can be at least 50%, at least 100%, at least 300%, at least 500%, at least 1,000%, at least 10,000%, at least 30,000%, at least 50,000%, at least 75,000%, at least 100,000%, at least 250,000%, at least 500,000%, at least 750,000%, at least 1,000,000%, at least 1,250,000%, at least 1,500,000%, at least 1,800,000%, at least 2,500,000%, at least 3,500,000%, or 4,140,000% greater than the time period the catalyst particles contact the hydrocarbon-containing feed to produce the conversion effluent.

Without wishing to be bound by theory, it is believed that at least a portion of the Group 8-10 element, e.g., Pt, disposed on the coked catalyst particles can be agglomerated as compared to the catalyst particles prior to contact with the hydrocarbon-containing feed. It is believed that during combustion of at least a portion of the coke on the coked catalyst particles that at least a portion of the Group 8-10 element can be re-dispersed about the support. Re-dispersing at least a portion of any agglomerated Group 8-10 element can increase the activity and improve the stability of the catalyst particles over many cycles.

In some embodiments, at least a portion of the Group 8-10 element, e.g., Pt, in the regenerated catalyst particles can be at a higher oxidized state as compared to the Group 8-10 element in the catalyst particles contacted with the hydrocarbon-containing feed and as compared to the Group 8-10 element in the coked catalyst particles. As such, as noted above, in some embodiments the process can optionally include contacting at least a portion of the regenerated catalyst particles with a reducing gas to produce regenerated and reduced catalyst particles. Suitable reducing gases (reducing agent) can be or can include, but are not limited to, molecular hydrogen, carbon monoxide, methane, ethane, ethylene, propane, propylene, steam, or a mixture thereof. In some embodiments, the reducing agent can be mixed with an inert gas such as argon, neon, helium, molecular nitrogen, or a mixture thereof. In such embodiments, at least a portion of the Group 8-10 element in the regenerated and reduced catalyst particles can be reduced to a lower oxidation state, e.g., the elemental state, as compared to the Group 8-10 element in the regenerated catalyst particles. In this embodiment, the additional quantity of the hydrocarbon-containing feed can be contacted with at least a portion of the regenerated catalyst particles and/or at least a portion of the regenerated and reduced catalyst particles.

In some embodiments, the regenerated catalyst particles and the reducing gas can be contacted at a temperature in a range from 400° C., 450° C., 500° C., 550° C., 600° C., 620° C., 650° C., or 670° C. to 720° C., 750° C., 800° C., or 900° C. The regenerated catalyst particles and the reducing gas can be contacted for a time period in a range from 1 second, 5 seconds, 10 seconds, 20 seconds, 30 seconds, or 1 minute to 10 minutes, 30 minutes, or 60 minutes. The regenerated catalyst particles and reducing gas can be contacted at a reducing agent partial pressure in a range from 20 kPa-absolute, 50 kPa-absolute, 70 kPa-absolute, 100 kPa-absolute, 150 kPa-absolute, or 200 kPa-absolute to 300 kPa-absolute, 500 kPa-absolute, 750 kPa-absolute, or 1,000 kPa-absolute.

In some embodiments, a first portion of the coked catalyst particles in the first particle stream rich in coked catalyst particles can be fed into the combustion zone for regeneration of the catalyst particles and a second portion of the coked catalyst particles can be recycled directly back into the conversion zone. In some embodiments, if the process includes both regeneration and reduction, a first portion of the coked catalyst particles in the first particle stream rich in coked catalyst particles can be fed into the combustion zone for regeneration of the catalyst particles and a second portion of the coked catalyst particles can be fed into the reduction zone. In other embodiments, if the process includes both regeneration and reduction, a first portion of the coked catalyst particles in the first particle stream rich in coked catalyst particles can be fed into the combustion zone for regeneration of the catalyst particles, a second portion of the coked catalyst particles can be recycled directly back into the conversion zone, and a third portion of the coked catalyst particles can be fed into the reduction zone. In any of these embodiments, on a continuous basis or intermittent basis, a portion of the coked catalyst particles, a portion of the regenerated catalyst particles, and/or a portion of the regenerated and reduced catalyst particles can be removed from the process and new or make-up catalyst particles can be introduced into the process. The removal of catalyst particles can be done as the catalyst particles break down in size, become inactivated, or begin to convert the hydrocarbon-containing feed at an undesirable rate of conversion.

At least a portion of the coked catalyst particles, at least a portion of the regenerated catalyst particles, at least apportion of the regenerated and reduced catalyst particles, new or make-up catalyst particles, or a mixture thereof can be contacted with the additional quantity of the hydrocarbon-containing feed within the conversion zone to produce the additional conversion effluent. As noted above, the cycle time from the contacting the hydrocarbon-containing feed with the catalyst particles to the contacting the additional quantity of the hydrocarbon-containing feed with at least a portion of the regenerated catalyst particles, and/or the regenerated and reduced catalyst particles, and optionally with new or make-up catalyst particles can be ≤70 minutes, e.g., from 1 minute to 70 minutes or 5 minutes to 45 minutes.

In some embodiments, one or more additional feeds, e.g., one or more stripping fluids, can be utilized to remove at least a portion of any entrained gaseous components from the catalyst particles. In some examples, the coked catalyst particles can be contacted with a stripping fluid prior to contact with the oxidant to remove at least a portion of any entrained upgraded hydrocarbons and/or molecular hydrogen, and/or other gaseous components. Similarly, the regenerated catalyst particles and/or the regenerated and reduced catalyst particles can be contacted with a stripping gas to remove at least a portion of any entrained combustion gas or reducing gas therefrom. In some embodiments, the stripping gas can be inert under the dehydrogenation, dehydroaromatization, and dehydrocyclization, combustion, and/or reducing conditions. Suitable stripping fluids can be or can include, but are not limited to, molecular nitrogen, helium, argon, carbon dioxide, steam, methane, or a mixture thereof.

The stripping gas can be contacted with the coked catalyst particles, the regenerated catalyst particles, and/or the regenerated and reduced catalyst particles at a volume ratio of about 0.1 m$^3$ to 10 m$^3$ of stripping gas per cubic meter of catalyst particles.

As noted above, the first cycle begins upon contact of the catalyst particles with the hydrocarbon-containing feed, followed by contact with at least the oxidant to produce the regenerated catalyst particles or at least the oxidant and the optional reducing gas to produce the regenerated and reduced catalyst particles, and the first cycle ends upon contact of the regenerated catalyst particles or the regenerated and reduced catalyst particles with the additional quantity of the hydrocarbon-containing feed. If any sweep fluid is utilized, e.g., to strip residual hydrocarbons from the coked catalyst particles, the time period such sweep fluid is utilized would be included in the cycle time. As such, the cycle time from the contacting the hydrocarbon-containing feed with the catalyst particles in step (I) to the contacting the additional quantity of the hydrocarbon-containing feed with the regenerated catalyst particles and/or the regenerated and reduced catalyst particles in step (V) can be ≤70 minutes, e.g., from 1 minute to 70 minutes or 5 minutes to 45 minutes.

In one embodiment, a riser configuration can be implemented in which the hydrocarbon-containing feed can be admixed with a dilution gas and contacted with heated and fluidized catalyst particles within the riser. The dilution gas can be or can include, but is not limited to, molecular nitrogen, methane, steam molecular hydrogen, or a mixture thereof. The combined gas can convect or otherwise convey the fluidized catalyst particles through the rise while contacting and reacting as the mixture flows through the riser to produce the conversion effluent that includes the upgraded hydrocarbons, molecular hydrogen, and the coked catalyst particles. A residence time of the hydrocarbon-containing feed and the fluidized catalyst particles can be sufficient to achieve a desired conversion of the hydrocarbon-containing feed to one or more upgraded hydrocarbons, the mixture can be separated through the use of a gas-solid separation device, where the gas can be sent for recovery and the catalyst particles can be recovered. The specific design of the riser, including fabrication and dimensions, can be dependent, at least in part, on the intended chemistry, but typically can require velocities in excess of 4.5 m/s under average gas composition. To reduce thermal cracking of the hydrocarbon, the conversion effluent can be quenched via one or more of a number of different methods after desired conversion of the hydrocarbon-containing feed is achieved but before solid-gas separation. Such methods include direct injection of a cooling medium such as steam into the conversion effluent, passing the conversion effluent through a heat exchanger, etc. The gaseous product after the gas-solid separation device can also be quenched using similar methods to avoid or reduce thermal cracking.

Systems suitable for carrying out the processes disclosed herein can include systems that are well-known in the art such as the fluidized reactors disclosed in U.S. Pat. Nos. 3,888,762; 7,102,050; 7,195,741; 7,122,160; and 8,653,317; U.S. Patent Application Publication Nos. 2004/0082824; 2008/0194891; and WO Publication Nos. WO$_{2001/85872}$; WO2004/029178; and WO2005/077867.

Catalyst Particles

The catalyst particles can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of the Group 8-10 element, based on the total weight of the support. In some embodiments, the catalyst particles can include ≤5.5 wt %, ≤4.5 wt %, ≤3.5 wt %, ≤2.5 wt %, ≤1.5 wt %, ≤1 wt %, ≤0.9 wt %, ≤0.8 wt %, ≤0.7 wt %, ≤0.6 wt %, ≤0.5 wt %, ≤0.4 wt %, ≤0.3 wt %, ≤0.2 wt %, ≤0.15 wt %, ≤0.1 wt %, ≤0.09 wt %, ≤0.08 wt %, ≤0.07 wt %, ≤0.06 wt %, ≤0.05 wt %, ≤0.04 wt %, ≤0.03 wt %, ≤0.02 wt %, ≤0.01 wt %, ≤0.009 wt %, ≤0.008 wt %, ≤0.007 wt %, ≤0.006 wt %, ≤0.005 wt %, ≤0.004 wt %, ≤0.003 wt %, or ≤0.002 wt % of the Group 8-10 element, based on the total weight of the support. In some embodiments, the catalyst particles can include >0.001 wt %, >0.003 wt %, >0.005 wt %, >0.007 wt %, >0.009 wt %, >0.01 wt %, >0.02 wt %, >0.025 wt %, >0.04 wt %, >0.05 wt %, >0.06 wt %, >0.07 wt %, >0.08 wt %, >0.09 wt %, >0.1 wt %, >0.13 wt %, >0.15 wt %, 0.17 wt %, >0.2 wt %, >0.2 wt %, >0.23, >0.25 wt %, >0.27 wt %, or >0.3 wt % and <0.5 wt %, <1 wt %, <2 wt %, <3 wt %, <4 wt %, <5 wt %, or <6 wt % of the Group 8-10 element based on the total weight of the support.

In some embodiments, the Group 8-10 element can be or can include, but is not limited to, Fe, Co, Ni, Ru, Pd, Os, Ir, Pt, a combination thereof, or a mixture thereof. In at least one embodiment, the Group 8-10 element can be or can include Pt. If two or more Group 8-10 elements are disposed on the support, the catalyst can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of a combined amount of the two or more Group 8-10 elements disposed on the support, based on the weight of the total weight of the support.

The support can be or can include, but is not limited to, one or more elements having an atomic number of 4, 12, 20-22, 30, 38-40, 48, or 56-71. Said another way, the support can be or can include one or more Group 2 elements, one or more Group 4 elements, one or more Group 12 elements, one or more elements having an atomic number of 21, 39, or 57-71, combinations thereof, or mixture thereof. In some embodiments, the Group 2 element, the Group 4 element, the Group 12 element, and/or the element having an atomic number of 21, 39, or 57-71 can be present in its elemental form. In other embodiments, the Group 2 element, the Group 4 element, the Group 12 element, and/or the element having an atomic number of 21, 39, or 57-71 can be present in the form of a compound. For example, the Group 2 element, the Group 4 element, the Group 12 element, and/or the element having an atomic number of 21, 39, or 57-71 can be present as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, a mixture of any two or more compounds that include the Group 2 element, the Group 4 element, the Group 12 element, and/or the element having an atomic number of 21, 39, or 57-71 can be present in different forms. For example, a first compound can be an oxide and a second compound can be an aluminate where the first compound and the second compound include the same or different Group 2 element, Group 4 element, Group 12 element, and/or element having an atomic number of 21, 39, or 57-71, with respect to one another.

In some embodiments, the support can be or can include at least one of: w wt % of the one or more Group 2 elements, x wt % of the one or more Group 4 elements, y wt % of the one or more Group 12 elements, and z wt % of the one or more elements having an atomic number of 21, 39, or 57-71 based on the weight of the support, where w, x, y, and z are independently in a range from 0 to 100, and where w+x+y+z is ≤100. Any Group 2 element present in the support can be associated with a wt % m based on the weight of the support, any Group 4 element present in the support can be associated with a wt % n based on the weight of the support, any Group 12 element present in the support can be associated with a wt % p based on the weight of the support, and any element having an atomic number of 21, 39, or 57-71 present in the support can be associated with a wt % q based on the weight of the support, where m, n, p, and q can independently be a number that is in a range from 1 to 100. In some embodiments, m, n, p, and q can each be equal to 1, 2, 15, or 30, or m can be equal to 1, n can be equal to 15, p can be equal to 15, and q can be equal to 1.

As used herein, "m" represents the minimum wt % of all Group 2 elements in the support, if none of the Group 4 elements, none of the Group 12 elements, and none of the elements having an atomic number of 21, 39, or 57-71 are present in the support. Similarly, as used herein, "n" represents the minimum wt % of all Group 4 elements in the support, if none of the Group 2 elements, none of the Group 12 elements, and none of the elements having an atomic number of 21, 39, or 57-71 are present in the support. Similarly, as used herein, "p" represents the minimum wt % of all Group 12 elements in the support, if none of the Group 2 elements, none of the Group 4 elements, and none of the elements having an atomic number of 21, 39, or 57-71 are present in the support, Finally, as used herein, "q" represents the minimum wt % of all elements having an atomic number of 21, 39, or 57-71 that are present in the support, if none of the Group 2 elements, none of the Group 4 elements, and none of the Group 12 elements are present in the support.

In some embodiments, a sum of w/m+x/n+y/p+z/q can be at least 1, based on the weight of the support. In other embodiments, a sum of w/m+x/n+y/p+z/q can be at least 1, at least 2, at least 4, at least 6, at least 8, at least 12, at least 24, at least 48, or at least 60, based on the weight of the support. In other embodiments, a sum of w/m+x/n+y/p+z/q can be in a range from 1, 2, 3, 4, 5, 6, 7, or 8 to 10, 12, 16, 24, 30, 48, or 60. In other embodiments, a sum of w/m+x/n+y/p+z/q can be in a range from 1 to 2, 2 to 4, 4 to 6, 6 to 8, 8 to 12, 12 to 24, 24 to 48, or 48 to 60.

As such, the m, n, p, and q not only specify the minimum amount of each group of elements present in the support when the other groups of elements are not present in the support, but also specify the minimum amount of each group of elements in the support when any one or more of the other groups of elements are also present in the support, which is explained by the following Example.

In this Example: m=4, n=8, p=12, q=20. If none of the Group 4 elements, none of the Group 12 elements, and none of the elements having an atomic number of 21, 39, or 57-71 are present in the support, then the total amount of any Group 2 element(s) in the support has to be ≥4 wt %, i.e., w/m ≥1. If none of the Group 2 elements, none of the Group 12 elements, and none of the elements having an atomic number of 21, 39, or 57-71 are present in the support, then the total amount of any Group 4 element(s) present in the support has to be ≥8 wt %, i.e., x/n≥1. If none of the Group 2 elements, none of the Group 4 elements, and none of the elements having an atomic number of 21, 39, or 57-71 are present in the support, then the total amount of any Group 12 element(s) present in the support has to be ≥12 wt %, i.e., y/p ≥1. If none of the Group 2 elements, none of the Group 4 elements, and none of the Group 12 elements exist on the support, then the total amount of any element(s) having an atomic number of 21, 39, or 57-71 present in the support has to be ≥20 wt %, i.e., z/q≥1.

If both Group 2 and 4 elements are present in the support and none of the Group 12 elements and none of the elements having an atomic number of 21, 39, or 57-71 are present in the support, then there is no need for the total amount of Group 2 element(s) to be ≥4 wt % since the Group 4 element(s) on the support share the role of the Group 2 element(s). Similarly, there is no need for the total amount of Group 4 element(s) to be ≥8 wt % since the Group 2 element(s) on the support share the role of the Group 4 element(s). Such an interchangeable relationship between the Group 2 and 4 elements is defined by m and n. Since m=4 and n=8, two mass units of the Group 4 element(s) interchanges one mass unit of the Group 2 element(s). For example, if the total amount of the Group 2 element(s) is w=1.1 wt % and the total amount of the Group 4 element(s) is x=4.3 wt %, then w/m+x/n=1.1/4+4.3/8=0.8125, which is <1, i.e., the total amount of the Group 2 and 4 elements is too little for the support to satisfy w/m+x/n+y/p+z/q is ≥1. In another example, if the total amount of the Group 2 element(s) is w=2.4 wt % and the total amount of the Group 4 element(s) is x=4.3 wt %, then w/m+x/n=2.4/4+4.3/8=1.1375, which is >1, such that the total amount of the Group 2 and Group 4 elements is sufficient to satisfy w/m+x/n+y/p+z/q is ≥1, despite that both w and x (2.4 and 4.3) are less than m and n (4 and 8), respectively.

The same principle also applies to cases when the support includes at least one element from three of the group of elements, e.g., Group 2, Group 4, and Group 12, as well as when the support includes each group of elements, i.e., at least one Group 2 element, at least one Group 4 element, at least one Group 12 element, and at least one element having an atomic number of 21, 39, or 57-71. For example, if the support includes 0.5 wt % of Mg (Group 2 element), 2 wt % of Ca (Group 2 element), 4 wt % of Ce (atomic number of 58), 3 wt % of Zr (Group 4 element), and 6 wt % of Zn (Group 12 element), then the equation would be: (0.5+2)/4+4/20+3/8+6/12=1.7, which is ≥1. In summary, m, n, p, and q is the minimum amount of each Group of elements in the support when the other Groups of elements are not present in the support. The equation w/m+x/n+y/p+z/q ≥1 defines how the 4 groups of elements can work together in the support.

In some embodiments, m can be one of ten values selected from: 2, 4, 6, 8, 10, 12, 14, 16, 18, and 20; n can be one of twelve values selected from: 2, 4, 6, 8, 10, 12, 14, 16, 18, 20, 22, and 24; p can be one of twelve values selected from: 2, 4, 6, 8, 10, 12, 14, 16, 18, 20, 22, and 24; and q can be one of twelve values selected from: 2, 4, 6, 10, 14, 18, 22, 26, 30, 34, 38, and 40, where m, n, p, and q can be any combination such that there are 17,280 (10×12×12×12) distinct combinations. In other embodiments, m can be equal to 2, 7, 10, or 20, n can be 2, 10, 20, or 25, p can be 2, 10, 20, or 25, and q can be 2, 10, 30, or 40, where m, n, p, and q can be any combination such that there are 256 (4×4×4×4) distinct combinations. In some embodiments, m, n, p, and q can each be equal to 2, 10, 15, or 30. In other embodiments, m can be equal to 7, n can be equal to 10, p can be equal to 10, and q can be equal to 10. In other embodiments, m can be equal to 7, n can be equal to 20, p can be equal to 20, and q can be equal to 10. In other embodiments, m can be equal to 10, n can be equal to 20, p can be equal to 20, and q can be equal to 30. In other embodiments, m can be equal to 7, n can be equal to 10, p can be equal to 10, and q can be equal to 30.

In some embodiments, w, x, y, and z can independently be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, where a sum of w, x, y, z is ≤100.

In some embodiments, when the support includes the Group 2 element, a molar ratio of the Group 2 element to the Group 8-10 element can be in a range from 0.24, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000, 300,000, 400,000, 500,000, 600,000, 700,000, 800,000, or 900,000. In some embodiments, when the support includes the Group 4 element, a molar ratio of the Group 4 element to the Group 8-10 element can be in a range from 0.18, 0.3, 0.5, 1, 10, 50, 100, 200, 300, 400, 500, 600, 700, 810, 1,000, or 5,000 to 10,000, 20,000, 30,000, 40,000, 50,000, 60,000, 70,000, or 81,000. In some embodiments, when the support includes the Group 12 element, a molar ratio of the Group 12 element to the Group 8-10 element can be in a range from 0.29, 0.5, 1, 10, 50, or 100 to 200, 300, 400, 500, 590, 600, or 1,000 to 5,000, 10,000, 20,000, 30,000, 40,000, 50,000 or 59,000. In some embodiments, when the support includes the element having an atomic number of 21, 39, or 57-71, a molar ratio of the element having an atomic number of 21, 39, or 57-71 to the Group 8-10 element can be in a range from 0.19, 0.5, 1, 10, 50, 100, or 150 to 200, 250, 300, 350, 400, 438, 500, 750, or 1,000 to 5,000, 10,000, 20,000, 30,000, 40,000, or 43,800. In some embodiments, when the support includes two or more of the Group 2, 4, or 12 element and the element having an atomic number of 21, 39, or 57-71, a molar ratio of a combined amount of any Group 2 element, any Group 4 element, any Group 12 element, and any element having an atomic number of 21, 39, or 57-71 to the Group 8-10 element can be in a range from 0.18, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 43,800, 45,000, 50,000, 55,000, 59,000, 60,000, 65,000, 70,000, 75,000, 80,000, 81,000, 85,000, 90,000, 95,000, 100,000, 200,000, 300,000, 400,000, 500,000, 600,000, 700,000, 800,000, or 900,000.

In some embodiments, the support can include ≥3 wt %, ≥6 wt %, ≥11 wt %, ≥15 wt %, ≥20 wt %, ≥25 wt %, ≥, 30 wt %, or ≥of a Group 2 element based on the weight of the support. In some embodiments, the Group 2 element can be or can include, but is not limited to, Mg. In some embodiments, the support can be or can include, but is not limited to, calcined hydrotalcite.

In some embodiments, the support can be or can include, but is not limited to, one or more of the following compounds: $Mg_uZn_{1-u}O$, where u is a positive number; $Zn_vAl2O3_{+v}$, where v is a positive number; $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number. BeO; MgO; CaO; BaO; SrO; $BeCO_3$; $MgCO_3$; $CaCO_3$; $SrCO_3$, $BaCO_3$; $ZrO_2$; ZrC; ZrN; $ZrSiO_4$; $CaZrO_3$; $Ca_7ZrAl_6O_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)2$; $Zn(ClO_3)_2$; $ZnSO_4$; $B_2O_6Zn_3$; $Zn_3N_2$; $ZnCO_3$; $CeO_2$; $Y_2O_3$; $La_2O_3$; $Sc_2O_3$; $Pr_6O_{11}$; $CePO_4$; $CeZrO_4$; $CeAlO_3$; $BaCeO_3$; $CePO_4$; Yttria-stabilized $ZrO_2$; one or more magnesium chromates, one or more magnesium tungstates, one or more magnesium molybdates combinations thereof, and mixtures thereof.

The $Mg_uZn_{1-u}O$, where u is a positive number, if present as the support or as a component of the support can have a molar ratio of Mg to Zn in a range from 1, 2, 3, or 6 to 12, 25, 50, or 100. The $Zn_vAl2O3_{+v}$, where v is a positive number, if present as the support or as a component of the support can have a molar ratio of Zn to Al in a range from 0.05, 0.3, or 0.6 to 0.9, 1.5, or 3 The $Mg_wAl_2O_{3+w}$, where w is a positive number, if present as the support or as a component of the support can have a molar ratio of Mg to Al in a range from 1, 2, 3, 4, or 5 to 6, 7, 8, 9, or 10. The $Ca_xAl_2O_{3+x}$, where x is a positive number, if present as the support or as a component of the support can have a molar ratio of Ca to Al in a range from 1:12, 1:4, 1:2, 2:3, 5:6, 1:1, 12:14, or 1.5:1. In some embodiments, the $Ca_xAl_2O_{3+x}$ can include tricalcium aluminate, dodecacalcium hepta-aluminate, moncalcium aluminate, moncalcium dialuminate, monocalcium hexa-aluminate, dicalcium aluminate, pentacalcium trialuminate, tetracalcium trialuminate, or any mixture thereof. The $Sr_yAl_2O_{3+y}$, where y is a positive number, if present as the support or as a component of the support can have a molar ratio of Sr to Al in a range from 0.05, 0.3, or 0.6 to 0.9, 1.5, or 3. The $Ba_zAl_2O_{3+z}$, where z is a positive number, if present as the support or as a component of the support can have a molar ratio of Ba to Al 0.05, 0.3, or 0.6 to 0.9, 1.5, or 3.

In some embodiments, the support can also include, but is not limited to, at least one metal element and/or at least one metalloid element selected from Groups 5, 6, 7, 11, 13, 14, 15, and 16 and/or at least one compound thereof. If the support also includes a compound that includes the metal element and/or metalloid element selected from Groups 5, 6, 7, 11, 13, 14, 15, and 16, the compound can be present in the support as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, suitable compounds that include the metal element and/or metalloid element selected from Groups 5, 6, 7, 11, 13, 14, 15, and 16 can be or can include, but are not limited to, one or more of the following: $B_2O_3$, $AlBO_3$, $Al_2O_3$, $SiO_2$, $SiC$, $Si_3N_4$, an aluminosilicate, $VO$, $V_2O_3$, $VO_2$, $V_2O_5$, $Ga_2O_3$, $In_2O_3$, $Mn_2O_3$, $Mn_3O_4$, $MnO$, one or more molybdenum oxides, one or more tungsten oxides, one or more zeolites, and mixtures and combinations thereof.

In some embodiments, the support can include the Group 2 element and Al and can be in the form of a mixed Group 2 element/Al metal oxide that has O, Mg, and Al atoms mixed on an atomic scale. In some embodiments the support can be or can include the Group 2 element and Al in the form of an oxide or one or more oxides of the Group 2 element and $Al_2O_3$ that can be mixed on a nm scale. In some embodiments, the support can be or can include an oxide of the Group 2 element, e.g., MgO, and $Al_2O_3$ mixed on a nm scale. In some embodiments, the support can be produced by calcining hydrotalcite.

In some embodiments, the support can be or can include a first quantity of the Group 2 element and Al in the form of a mixed Group 2 element/Al metal oxide and a second quantity of the Group 2 element in the form of an oxide of the Group 2 element. In such embodiment, the mixed Group 2 element/Al metal oxide and the oxide of the Group 2 element can be mixed on the nm scale and the Group 2 element and Al in the mixed Group 2 element/Al metal oxide can be mixed on the atomic scale.

In other embodiments, the support can be or can include a first quantity of the Group 2 element and a first quantity of Al in the form of a mixed Group 2 element/Al metal oxide, a second quantity of the Group 2 element in the form of an oxide of the Group 2 element, and a second quantity of Al in the form of $Al_2O_3$. In such embodiment, the mixed Group 2 element/Al metal oxide, the oxide of the Group 2 element, and the $Al_2O_3$ can be mixed on a nm scale and the Group 2 element and Al in the mixed Group 2 element/Al metal oxide can be mixed on the atomic scale.

In some embodiments, when the support includes the Group 2 element and Al, a weight ratio of the Group 2 element to the Al in the support can be in a range from 0.001, 0.005, 0.01, 0.05, 0.1, 0.15, 0.2, 0.3, 0.5, 0.7, or 1 to 3, 6, 12.5, 25, 50, 75, 100, 200, 300, 400, 500, 600, 700, 800, 900, or 1,000. In some embodiments, when the support includes Al, the support can include Al in a range from 0.5 wt %, 1 wt %, 1.5 wt %, 2 wt %, 2.1 wt %, 2.3 wt %, 2.5 wt %, 2.7 wt %, 3 wt %, 4 wt %, 5 wt %, 6 wt %, 7 wt %, 8 wt %, 9 wt %, 10 wt %, or 11 wt % to 15 wt %, 20 wt %, 25 wt %, 30 wt %, 40 wt %, 45 wt %, or 50 wt %, based on the weight of the support.

In some embodiments, the support can also include one or more promoters disposed thereon. The promoter can be or can include, but is not limited to, Sn, Ga, Zn, Ge, In, Re, Ag, Au, Cu, a combination thereof, or a mixture thereof. As such, the promoter if present as a component of the catalyst particles, can be present as a component of the support, as a promoter disposed on the support, or both as a component of the support and as a promoter disposed on the support. In some embodiments, the promoter can be associated with the Group 8-10 element, e.g., Pt. For example, the promoter and the Group 8-10 element disposed on the support can form Group-8-10 element-promoter clusters that can be dispersed on the support. The promoter, if present, can improve the selectivity/activity/longevity of the catalyst for a given upgraded hydrocarbon. In some embodiments, the addition of the promoter can improve the propylene selectivity of the catalyst particles when the hydrocarbon-containing feed includes propane. The catalyst particles can include the promoter in an amount of 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 3 wt %, 5 wt %, 7 wt %, or 10 wt %, based on the weight of the support.

In some embodiments, the support can also include one or more alkali metal elements disposed on the support. The alkali metal element, if present, can be or can include, but is not limited to, Li, Na, K, Rb, Cs, a combination thereof, or a mixture thereof. In at least some embodiments, the alkali metal element ca be or can include K and/or Cs. The alkali metal element, if present, can improve the selectivity of the catalyst particles for a given upgraded hydrocarbon. The catalyst particles can include the alkali metal element in an amount 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, or 5 wt %, based on the weight of the support.

The preparation of the support can be accomplished via any known process. For simplicity and ease of description, the preparation of a suitable support that includes a mixed oxide of magnesium and aluminum (Mg(Al)O or MgO/$Al_2O_3$) support will be described in more detail. Catalyst synthesis techniques are well-known and the following description is for illustrative purposes and not to be considered as limiting the synthesis of the support or the catalyst particles. In some embodiments, to make the MgO/$Al_2O_3$ mixed oxide support, Mg and Al precursors such as $Mg(NO_3)_2$ and $Al(NO_3)_3$ can be mixed together, e.g., ball-milled, followed by calcination to produce the support. In another embodiment, the two precursors can be dissolved in $H_2O$, stirred until dry (with heat optionally applied), followed by calcination to produce the support. In another embodiment, the two precursors can be dissolved in $H_2O$, followed by the addition of a base and a carbonate, e.g., NaOH/$Na_2CO_3$ to produce hydrotalcite, followed by calcination to produce the support. In another embodiment, a commercial ready MgO and $Al_2O_3$ may be mixed and ball-milled. In another embodiment, the Mg(NO$_3$)$_2$ precursor can be dissolved in H$_2$O and the solution can be impregnated onto an existing support, e.g., an Al$_2$O$_3$ support, that can be dried and calcined to produce the support. In another embodiment, Mg from Mg(NO$_3$)$_2$ can be loaded onto an existing Al$_2$O$_3$ support through ion adsorption, followed by liquid-solid separation, drying and calcination to produce the support. Without wishing to be bound by theory, it is believed that the inorganic support produced via any one of the above methods and/or other methods can include (i) the Mg and Al mixed together on the nm scale, (ii) the Mg and Al in the form of a mixed Mg/Al metal oxide, or (iii) a combination of (i) and (ii).

Group 8-10 metals and any promoter and/or any alkali metal element may be loaded onto the mixed oxide support by any known technique. For example, one or more Group 8-10 element precursors, e.g., chloroplatinic acid, tetramineplatinum(II) nitrate, and/or tetramineplatinum(II) hydroxide, one or more promoter precursors (if used), e.g., a salt such as SnCl$_4$ and/or AgNO$_3$, and one or more alkali metal element precursors (if used), e.g., KNO$_3$, KCl, and/or NaCl, can be dissolved in water. In some embodiments, the Group 8-10 element precursor can be or can include, but is not limited to, chloroplatinic acid hexahydrate, tetraammineplatinum(II) nitrate, platinum(II) oxalate, platinum(II) acetylacetonate, platinum(II) bromide, platinum(II) iodide, platinum(II) chloride, platinum(IV) chloride, platinum(II) diammine dichloride, ammonium tetrachloroplatinate(II), tetraammineplatinum(II) chloride hydrate, tetraammineplatinum(II) hydroxide hydrate, iron nitrate, rhodium(III) nitrate, ruthenium(III) nitrate, cobalt(II) nitrate hexahydrate, nickel(II) nitrate hexahydrate, palladium(II) nitrate dihydrate, or any mixture thereof. In some embodiments, the promoter precursor can be or can include, but is not limited to, tin(II) oxide, tin(IV) oxide, tin(IV) chloride pentahydrate, tin(II) chloride dihydrate, tin citrate, tin sulfate, tin oxalate, tin(II) bromide, tin(IV) bromide, tin(II) acetylacetonate, tin(II) acetate, tin(IV) acetate, silver(I) nitrate, gold(III) nitrate, copper(II) nitrate, gallium(III) nitrate, or any mixture thereof. In some embodiments, the alkali metal element precursor can be or can include, but is not limited to, lithium nitrate, sodium nitrate, potassium nitrate, rubidium nitrate, cesium nitrate, or any mixture thereof.

The solution can be impregnated onto the support, followed by drying and calcination to produce the catalyst. In some embodiments, the Group 8-10 element precursor and optionally the promoter precursor and/or the alkali metal element precursor can be loaded onto the support at the same time, or separately in a sequence separated by drying and/or calcination steps to produce the catalyst. In other embodiments, the Group 8-10 element and, optionally the promoter and/or alkali metal element, can be loaded onto the support by chemical vapor deposition, where the precursors are volatilized and deposited onto the support, followed by calcination to produce the catalyst. In other embodiments, the Group 8-10 element precursor and, optionally, the promoter precursor and/or alkali metal precursor, can be loaded onto the support through ion adsorption, followed by liquid-solid separation, drying and calcination to produce the catalyst. Optionally, the catalyst particles can also be synthesized using a one-pot synthesis method where the precursors of the support, group 8-10 metal active phase and the promoters are all mixed together, dry or wet, with or without any other additives to aid the synthesis, followed by drying and calcination to produce the catalyst. In some embodiments, the drying or calcination may be carried out in an oxidative environment, or a reductive environment, or an inert environment, or a combination of two or more of the environments. In some embodiments, a suitable oxidative environment can be provided by air, enriched air, O$_2$, O$_2$ diluted by one or more inert gases, O$_3$, O$_3$ diluted by one or more inert gases, or any mixture thereof. In some embodiments, a suitable reductive environment can be provided by H$_2$, CO, syngas, or any reductive gas diluted by one or more inert gases. In some embodiments, a suitable inert environment can be provided by steam, N$_2$, Ar, He, or any mixture of the above. While drying/calcination is typically accompanied by the release of one or more volatiles, in some embodiments, the drying/calcination step can be preceded by an equilibration step where no release of volatiles is expected. For example, equilibration may be conducted at room temperature in air for a period of 10 min, 30 min, 60 min, or 120 min. Drying may be conducted at a temperature between room temperature to 400° C. either in air or in vacuum for a period of 10 min, 30 min, 60 min, or 120 min. Calcination may be conducted at a temperature of 400-850° C. in air for a period of 10 min, 30 min, 60 min, or 120 min. Alternatively, calcination may be conducted at 400-850° C. in air for a period of 10 min, 30 min, 60 min, or 120 min (denoted as O), followed by a hydrogen treatment at 400-850 C for a period of 10 min, 30 min, 60 min, or 120 min (denoted as R). In some cases, O and R may be cycled, for example, an O—R—O—R, or an R—O—R—O, or an O—R—O process may be employed for calcination.

Suitable processes that can be used to prepare the catalyst particles disclosed herein can include the processes described in U.S. Pat. Nos. 4,788,371; 4,962,265; 5,922,925; 8,653,317; EP Patent No. EP0098622; Journal of Catalysis 94 (1985), pp. 547-557; and/or Applied Catalysis 54 (1989), pp. 79-90.

The as-synthesized catalyst particles, when examined under scanning electron microscope or transmission electron microscope, can appear as either primary particles, as agglomerates of primary particles, as aggregates of primary particles, or a combination thereof. Primary particles, agglomerates of primary particles and aggregates of primary particles are described in Powder Technology 181 (2008) 292-300. The primary particles in the as-synthesized catalyst particles, when examined under scanning electron microscope or transmission electron microscope, can have an average cross-sectional length or average particle size, e.g., a diameter when spherical, in a range from 0.2 nm, 0.5 nm, 1 nm, 5 nm, 10 nm, 25 nm, 30 nm, 40 nm 50 nm, 60 nm, 70 nm, 80 nm, 90 nm, 100 nm, 150 nm, 200 nm, 250 nm, 300 nm, 350 nm, 400 nm, 450 nm, or 500 nm to 1 μm, 10 μm, 25 μm, 50 μm, 100 μm, 150 μm, 200 μm, 250 μm, 300 μm, 400 μm, or 500 μm. In some embodiments, the primary particles in the as-synthesized catalyst particles can have an average particle size of 0.2 nm to 500 μm, 0.5 nm to 300 μm, 1 nm to 200 μm, 2 nm to 100 μm, 2 nm to 500 nm, or 2 nm to 100 nm, as measured by a transmission electron microscope.

The as-synthesized catalyst particles can have a surface area in a range from 0.1 m$^2$/g, 1 m$^2$/g, 10 m$^2$/g, or 100 m$^2$/g to 500 m$^2$/g, 800 m$^2$/g, 1,000 m$^2$/g, or 1,500 m$^2$/g. The surface area of the catalyst particles can be measured according to the Brunauer-Emmett-Teller (BET) method using adsorption-desorption of nitrogen (temperature of liquid nitrogen, 77 K) with a Micromeritics 3flex instrument after degassing of the powders for 4 hours at 350° C. More information regarding the method can be found, for example, in "Characterization of Porous Solids and Powders: Surface Area, Pore Size and Density," S. Lowell et al., Springer, 2004.

The as-synthesized catalyst particles can be formulated into one or more appropriate forms for different short cycle (≤70 minutes) hydrocarbon upgrading processes. Alternatively, the support can be formulated into appropriate forms for different short cycle hydrocarbon upgrading processes, before the addition of the Group 8-10 element and, any optional promoter and/or alkali metal element. During formulation, one or more binders and/or additives can be added to the catalyst particles and/or support to improve the chemical/physical properties of the catalyst particles ultimately produced and used in the process. The binder/additives can be or can include, but is not limited to, silica, silica sol, silica-alumina, alumina, aluminum chlorhydrol, peptized alumina, aluminosilicates, smectites, kaolins, acid-treated metakaolins, illites, chlorites, attapulgites, pillared interlayered clays and mixed layer clays, silanes, alkoxysilanes, aryloxysilanes, acyloxysilanes, oximinosilanes, halosilanes, aminoxysilanes, aminosilanes, amidosilanes, silazanes, silicones, or a mixture thereof.

In some embodiments, the catalyst particles can be formulated via the well-known spray drying process. Spray-dried catalyst particles having an average cross-sectional area in a range from 20 μm, 40 μm, or 50 μm to 80 μm, 90 μm, or 100 μm are typically used in an FCC type fluid—bed reactor. To make spray-dried catalyst particles, the support, the Group 8-10 element, and any additional components, e.g., the promoter and/or the alkali metal, can be made into a slurry with binder/additive in the slurry before spray-drying and calcination. Alternatively, the Group 8-10 element, and any additional components, e.g., the promoter and/or the alkali metal, can be added to the formulated support to produce the formulated catalyst.

The formulated catalyst particles can have a particle density in a range from 0.5 g/cm$^3$, 0.7 g/cm$^3$, 0.9 g/cm$^3$, 1 g/cm$^3$, 1.2 g/cm$^3$, or 1.3 g/cm$^3$, to 1.5 g/cm$^3$, 1.8 g/cm$^3$, 2 g/cm$^3$, 2.3 g/cm$^3$, 2.5 g/cm$^3$, 2.7 g/cm$^3$, or 3 g/cm$^3$. The "particle density" refers to the density of the catalyst particles including the pore volume in g/cm$^3$ and can be measured by mercury porosimetry. The particle density of the catalyst particles can be measured according to UOP578-11. In some embodiments, the catalyst particles can have an average particle size and particle density consistent with a Geldart A definition.

Hydrocarbon-Containing Feed

The $C_2$-$C_{16}$ alkanes can be or can include, but are not limited to, ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, or a mixture thereof. For example, the hydrocarbon-containing feed can include propane, which can be dehydrogenated to produce propylene, and/or isobutane, which can be dehydrogenated to produce isobutylene. In another example, the hydrocarbon-containing feed can include liquid petroleum gas (LP gas), which can be in the gaseous phase when contacted with the catalyst particles. In some embodiments, the hydrocarbon in the hydrocarbon-containing feed can be composed of substantially a single alkane such as propane. In some embodiments, the hydrocarbon-containing feed can include ≥50 mol %, ≥75 mol %, ≥95 mol %, ≥98 mol %, or ≥99 mol % of a single $C_2$-$C_{16}$ alkane, e.g., propane, based on a total weight of all hydrocarbons in the hydrocarbon-containing feed. In some embodiments, the hydrocarbon-containing feed can include at least 50 vol %, at least 55 vol %, at least 60 vol %, at least 65 vol %, at least 70 vol %, at least 75 vol %, at least 80 vol %, at least 85 vol %, at least 90 vol %, at least 95 vol %, at least 97 vol %, or at least 99 vol % of a single $C_2$-$C_{16}$ alkane, e.g., propane, based on a total volume of the hydrocarbon-containing feed.

The $C_8$-$C_{16}$ alkyl aromatic hydrocarbons can be or can include, but are not limited to, ethylbenzene, propylbenzene, butylbenzene, one or more ethyl toluenes, or a mixture thereof. In some embodiments, the hydrocarbon-containing feed can include ≥50 mol %, ≥75 mol %, ≥95 mol %, ≥98 mol %, or ≥99 mol % of a single $C_8$-$C_{16}$ alkyl aromatic, e.g., ethylbenzene, based on a total weight of all hydrocarbons in the hydrocarbon-containing feed. In some embodiments, the ethylbenzene can be dehydrogenated to produce styrene. As such, in some embodiments, the processes disclosed herein can include propane dehydrogenation, butane dehydrogenation, isobutane dehydrogenation, pentane dehydrogenation, pentane dehydrocyclization to cyclopentadiene, naphtha reforming, ethylbenzene dehydrogenation, ethyltoluene dehydrogenation, and the like.

In some embodiments, the hydrocarbon-containing feed can be diluted with one or more diluents gases. Suitable diluents can be or can include, but are not limited to, argon, neon, helium, molecular nitrogen, carbon dioxide, methane, molecular hydrogen, or a mixture thereof. If the hydrocarbon containing-feed includes a diluent, the hydrocarbon-containing feed can include 0.1 vol %, 0.5 vol %, 1 vol %, or 2 vol % to 3 vol %, 8 vol %, 16 vol %, or 32 vol % of the diluent, based on a total volume of any $C_2$-$C_{16}$ alkanes and any $C_8$-$C_{16}$ alkyl aromatic hydrocarbons in the hydrocarbon-containing feed. When the diluent includes molecular hydrogen, a molar ratio of the molecular hydrogen to a combined amount of any $C_2$-$C_{16}$ alkane and any $C_8$-$C_{16}$ alkyl aromatic hydrocarbons can be in a range from 0.1, 0.3, 0.5, 0.7, or 1 to 2, 3, 4, 5, 6, 7, 8, 9, or 10. In some embodiments, if the diluent is used, the diluent can be mixed with the hydrocarbon-containing feed and/or introduced or otherwise fed into the conversion zone as a separate feed via one or more inlets dedicated to feeding the diluent into the conversion zone. Similarly, the hydrocarbon-containing feed can also be introduced into the conversion zone via one or more inlets dedicated to feeding the hydrocarbon-containing feed into the conversion zone.

In some embodiments, the hydrocarbon-containing feed can be substantially free of any steam, e.g., <0.1 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include steam. For example, the hydrocarbon-containing feed can include 0.1 vol %, 0.3 vol %, 0.5 vol %, 0.7 vol %, 1 vol %, 3 vol %, or 5 vol % to 10 vol %, 15 vol %, 20 vol %, 25 vol %, 30 vol %, 35 vol %, 40 vol %, 45 vol %, or 50 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include ≤50 vol %, ≤45 vol %, ≤40 vol %, ≤35 vol %, ≤30 vol %, ≤25 vol %, ≤20 vol %, or ≤15 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include at least 1 vol %, at least 3 vol %, at least 5 vol %, at least 10 vol %, at least 15 vol %, at least 20 vol %, at least 25 vol %, or at least 30 vol % of steam, based on a total volume of any $C_2$-$C_{16}$ alkanes and any $C_8$-$C_{16}$ alkyl aromatic hydrocarbons in the hydrocarbon-containing feed. Similar to the diluent, if steam is fed into the conversion zone, the steam can be fed into the conversion zone as a component of the hydrocarbon-containing feed or via one or more separate inlets dedicated to introducing the steam into the conversion zone.

In some embodiments, the hydrocarbon-containing feed can include sulfur. For example, the hydrocarbon-containing feed can include sulfur in a range from 0.5 ppm, 1 ppm, 5 ppm, 10 ppm, 20 ppm 30 ppm, 40 ppm, 50 ppm, 60 ppm, 70 ppm, or 80 ppm to 100 ppm, 150 ppm, 200 ppm, 300 ppm, 400 ppm, or 500 ppm. In other embodiments, the hydrocarbon-containing feed can include sulfur in a range from 1 ppm to 10 ppm, 10 ppm to 20 ppm, 20 ppm to 50 ppm, 50 ppm to 100 ppm, or 100 ppm to 500 ppm. The sulfur, if present in the hydrocarbon-containing feed, can be or can include, but is not limited to, $H_2S$, dimethyl disulfide, as one or more mercaptans, or any mixture thereof. In some embodiments, the sulfur can be introduced into the conversion zone as a separate feed, as a component of the diluent if used, and/or as a component of the steam if used.

The hydrocarbon-containing feed can be substantially free or free of molecular oxygen. In some embodiments, the hydrocarbon-containing feed can include ≤5 mol %, ≤3 mol %, or ≤1 mol % of molecular oxygen ($O_2$). It is believed that providing a hydrocarbon-containing feed substantially-free of molecular oxygen substantially prevents oxidative coupling reactions that would otherwise consume at least a portion of the alkane and/or the alkyl aromatic hydrocarbon in the hydrocarbon-containing feed.

Recovery and Use of the Upgraded Hydrocarbons

The upgraded hydrocarbon can include at least one upgraded hydrocarbon, e.g., an olefin, water, unreacted hydrocarbons, unreacted molecular hydrogen, etc. The upgraded hydrocarbon can be recovered or otherwise obtained via any convenient process, e.g., by one or more conventional processes. One such process can include cooling the effluent to condense at least a portion of any water and any heavy hydrocarbon that may be present, leaving the olefin and any unreacted alkane or alkyl aromatic primarily in the vapor phase. Olefin and unreacted alkane or alkyl aromatic hydrocarbons can then be removed from the reaction product in one or more separator drums. For example, one or more splitters can be used to separate the dehydrogenated product from the unreacted hydrocarbon-containing feed.

In some embodiments, a recovered olefin, e.g., propylene, can be used for producing polymer, e.g., recovered propylene can be polymerized to produce polymer having segments or units derived from the recovered propylene such as polypropylene, ethylene-propylene copolymer, etc. Recovered isobutene can be used, e.g., for producing one or more of: an oxygenate such as methyl tert-butyl ether, fuel additives such as diisobutene, synthetic elastomeric polymer such as butyl rubber, etc.

Exemplary Embodiments

FIG. 1 depicts a system for upgrading a hydrocarbon-containing feed in line 20 that includes a reactor or conversion zone 1 and a regenerator or combustion zone 2, according to one or more embodiments. The hydrocarbon-containing feed via line 20 can be introduced into the reactor 1, e.g., at a bottom end of a riser reactor or an upper end of a downer reactor. In some embodiments, a diluent gas via line 21 can be mixed with the hydrocarbon-containing feed in line 20. The hydrocarbon-containing feed and optional diluent gas can be mixed or otherwise contacted with regenerated catalyst particles introduced via line 50 into the reactor 1. The regenerated catalyst particles in line 50 can be moved or otherwise conveyed through line 50 via a transport gas introduced via line 31. As the hydrocarbon-containing feed reacts in the presence of the catalyst particles and moves through the reactor 1, additional hydrocarbon-containing feed via line 22 and/or additional diluent gas via line 23 can optionally be introduced into the reactor 1. The gaseous components and coked catalyst particles can be separated via one or more gas-solid separation devices, as previously described, with a first gaseous stream rich in the one or more upgraded hydrocarbons, unreacted hydrocarbons, molecular hydrogen, and any other gaseous components recovered via line 24 and a first particle stream rich in coked catalyst particles recovered via line 51. While the separation of the gaseous components and the coked catalyst particles is shown as occurring within the reactor 1, such separation can also occur outside of reactor 1.

The first gaseous stream via line 24 can be sent to product recovery and subjected to additional processing steps. The first particle stream rich in the coked catalyst particles can be introduced via line 51 into the regenerator 2. The regenerator 2 can be a reactor where the coked catalyst particles can be contacted with an oxidant, e.g., air, introduced via line 25 to combust at least a portion of the coke deposited on the surface of the catalyst particles. In some embodiments, an optional supplemental fuel via line 26 can also be introduced into the regenerator 2. The supplemental fuel can be used to produce additional heat that can further heat the regenerated catalyst particles within the regenerator 2 to a desired temperature to support the endothermic reactions that occur within the reactor 1.

Within regenerator 2, a gas-solid separation device can be used to separate the regenerated catalyst particles from the combustion gas with a second gaseous steam rich in the combustion gas recovered via line 27 and a second particle stream rich in the regenerated catalyst particles recovered via line 50. In some embodiments, the combustion gas in line 27, which may contain fine catalyst particulates, can be directed to a secondary separation device for recovery of the fine catalyst particulates, heat recovery, or disposal. The regenerated catalyst particles can be introduced via line 50 into the reactor 1 with the transport gas via line 31 used to convey the catalyst particles into the reactor 1.

Figure 2:
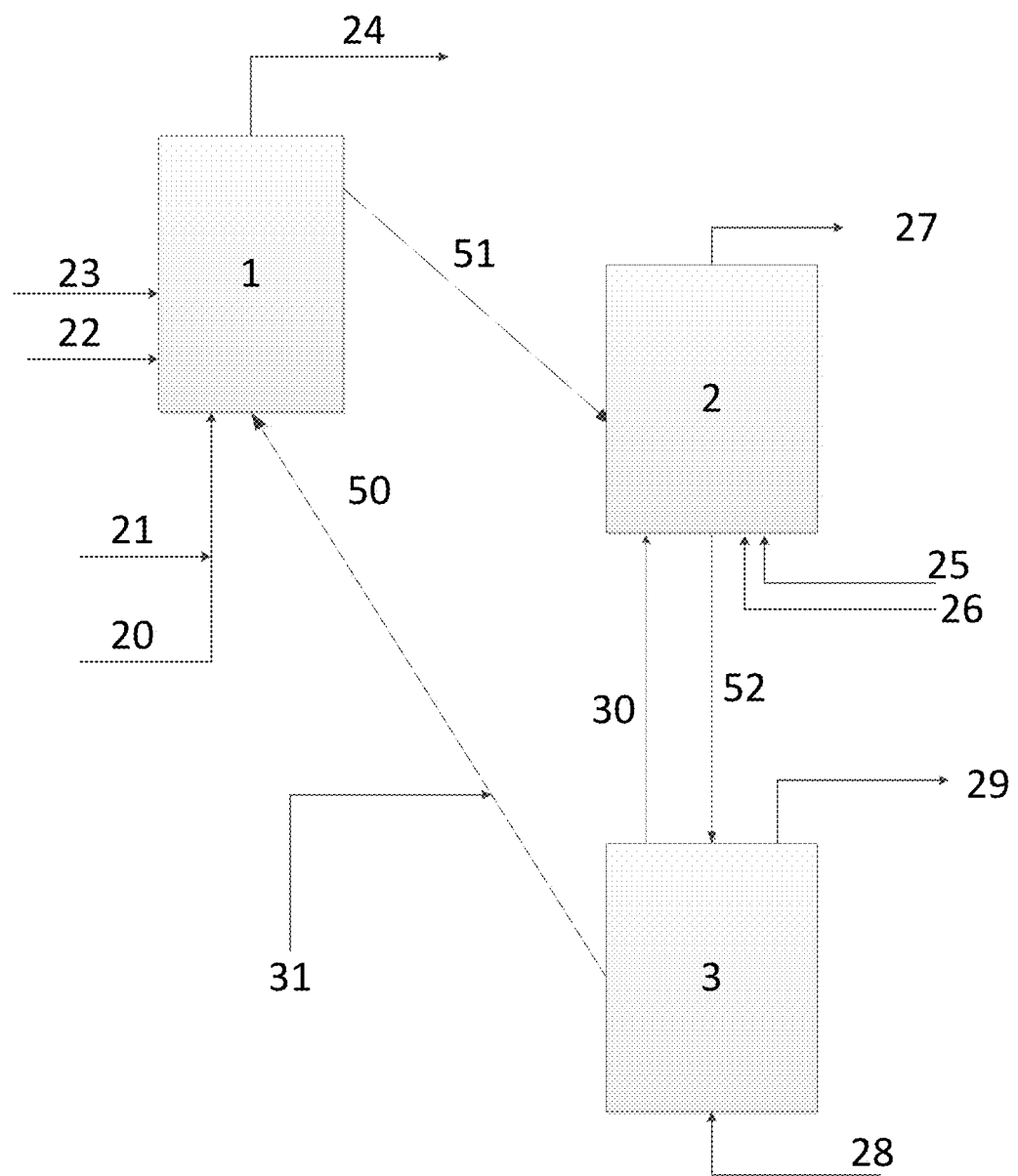
FIG. 2 depicts another system for upgrading the hydrocarbon-containing feed that includes a reactor, a regenerator, and a reduction reactor, according to one or more embodiments described.

FIG. 2 depicts another system for upgrading the hydrocarbon-containing feed in line 20 that includes the reactor or conversion zone 1, the regenerator or combustion zone 2, and a reduction reactor or reduction zone 3, according to one or more embodiments. The hydrocarbon-containing feed via line 20 can be introduced into the reactor 1, e.g., at a bottom end of a riser reactor or an upper end of a downer reactor. In some embodiments, a diluent gas via line 21 can be mixed with the hydrocarbon-containing feed in line 20. The hydrocarbon-containing feed and optional diluent gas can be mixed or otherwise contacted with regenerated and reduced catalyst particles introduced via line 50 into the reactor 1. The regenerated and reduced catalyst particles in line 50 can be moved or otherwise conveyed through line 50 via a transport gas introduced via line 31. As the hydrocarbon-containing feed reacts in the presence of the catalyst particles and moves through the reactor 1, additional hydrocarbon-containing feed via line 22 and/or additional diluent gas via line 23 can optionally be introduced into the reactor 1. The gaseous components and coked catalyst particles can be separated via one or more gas-solid separation devices, as previously described, with a first gaseous stream rich in the one or more upgraded hydrocarbons, unreacted hydrocarbons, molecular hydrogen, and any other gaseous components recovered via line 24 and a first particle stream rich in coked catalyst particles recovered via line 51.

The first gaseous stream via line 24 can be sent to product recovery and subjected to additional processing steps. The first particle stream rich in the coked catalyst particles can be introduced via line 51 into the regenerator 2. The regenerator 2 can be a reactor where the coked catalyst particles can be contacted with an oxidant, e.g., air, introduced via line 25 to combust at least a portion of the coke deposited on the surface of the catalyst particles. As required, a supplemental fuel via line 26 can also be introduced into the regenerator 2. The supplemental fuel can be used to further heat the regenerated catalyst particles within the regenerator 2 to a desired temperature to support the endothermic reactions that occur within the reactor 1.

Within the regenerator 2, a gas-solid separation device can be used to separate the regenerated catalyst particles from the combustion gas with a second gaseous stream rich in the combustion gas recovered via line 27 and a second particle stream rich in the regenerated catalyst particles recovered via line 52. In some embodiments, the combustion gas in line 27, which may contain fine catalyst particulates, can be directed to a secondary separation device for recovery of fine catalyst particulates, heat recovery, or disposal.

The regenerated catalyst particles via line 52 and a reducing gas via line 28 can be introduced into the reduction reactor 3. The regenerated catalyst particles can be contacted with the reducing gas within the reduction reactor 3 to produce regenerated and reduced catalyst particles. Within the reduction reactor 3, a gas-solid separation device may be used to separate the regenerated and reduced catalyst particles from the reducing gas with a third gaseous stream rich in the reducing gas recovered via line 30 and/or line 29 and a third particle stream rich in the regenerated and reduced catalyst particles via line 50. Depending, at least in part, on the composition of the reducing gas, the reducing gas, in whole or in part, can be introduced via line 30 into the regenerator 2 to provide at least a portion of the optional supplemental fuel that can be fed into the regenerator 2. In some embodiments, the reducing gas can be removed via line 29 from the system. In some embodiments, the residual reducing gas and the gaseous products from catalyst reduction may be carried directly into reactor 1 without being separated from the catalyst. The regenerated and reduced catalyst particles can be introduced via line 50 into the reactor 1, with the transport gas via line 31 used to convey the catalyst particles into the reactor 1.

Figure 3:
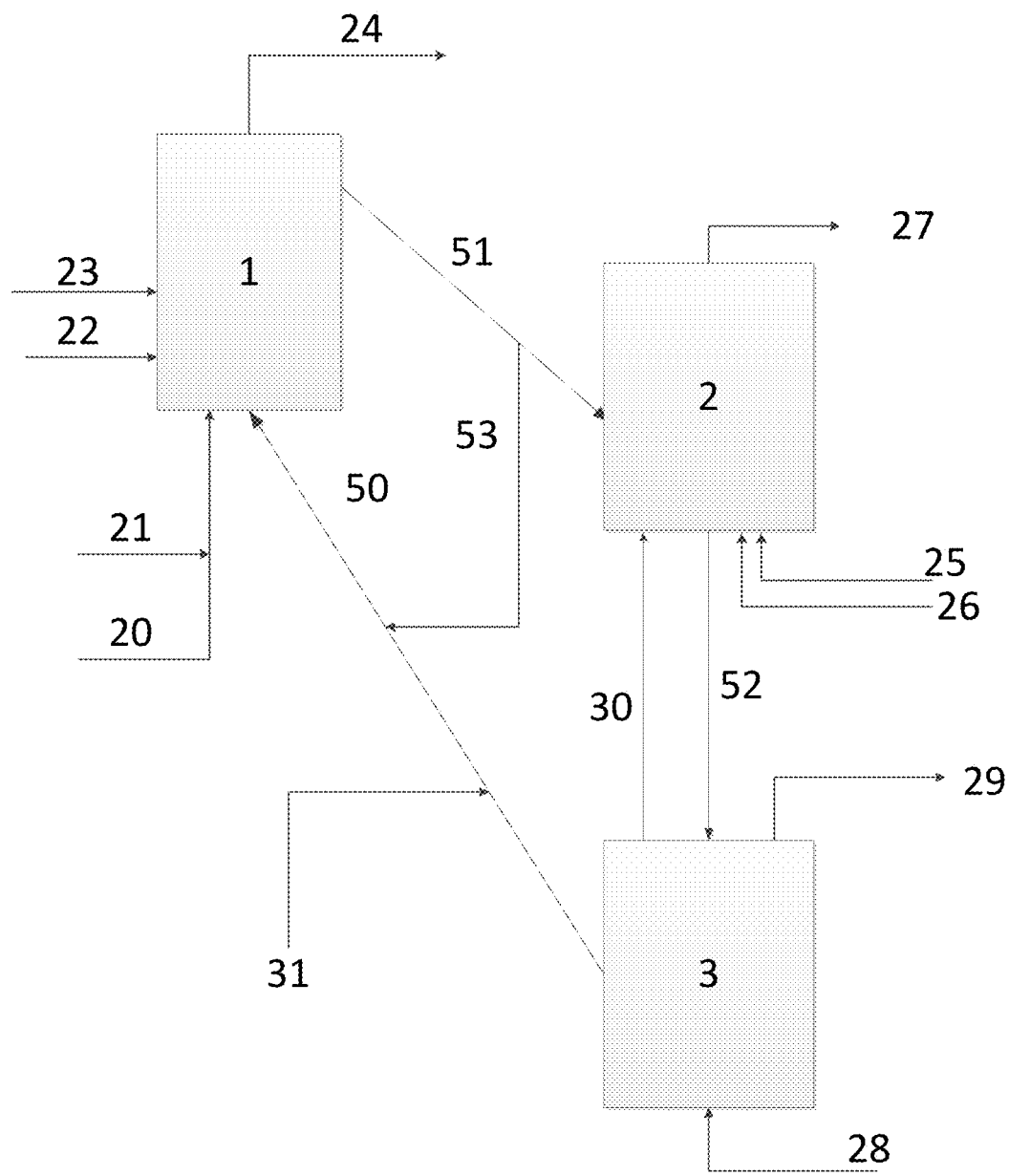
FIG. 3 depicts another system for upgrading the hydrocarbon-containing feed that includes a reactor, a regenerator, a reduction reactor, and a recycle line for recycling at least a portion of the coked catalyst particles into the reactor, according to one or more embodiments described.

FIG. 3 depicts another system for upgrading the hydrocarbon-containing feed in line 20 that includes the reactor or conversion zone 1, the regenerator or combustion zone 2, the reduction reactor or reduction zone 3, and a recycle line 53 for recycling at least a portion of the coked catalyst particles in line 51 into the reactor 1, according to one or more embodiments. In some embodiments, the extent of catalyst deactivation within reactor 1 may not be sufficient to necessitate introducing all the coked catalyst particles into the regenerator 2. As such, recycling at least a portion of the coked catalyst particles into the reactor 1 can be carried out to reduce or minimize the amount of catalyst particles introduced into the regenerator.

Figure 4:
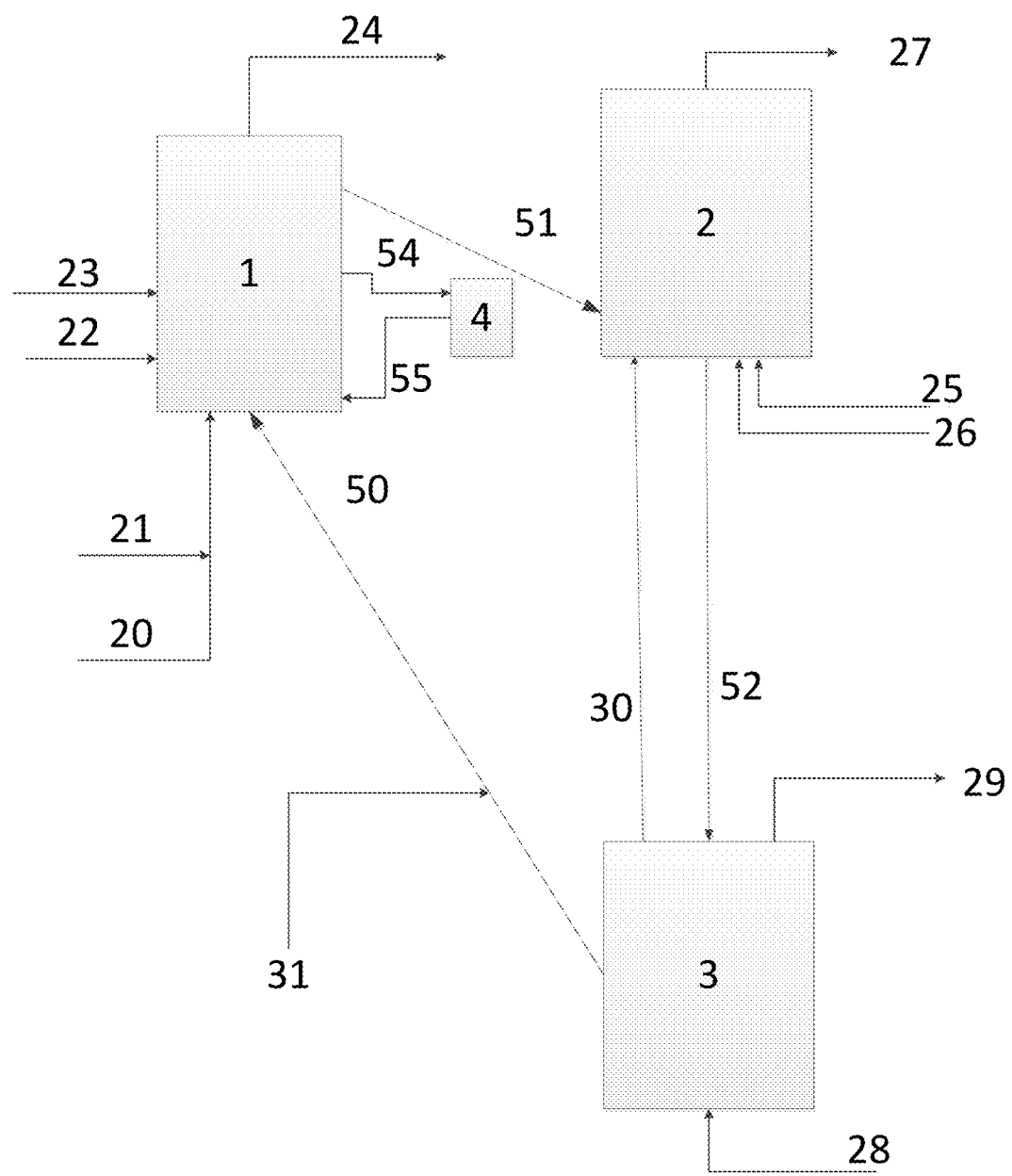
FIG. 4 depicts another system for upgrading the hydrocarbon-containing feed that includes a reactor, a regenerator, a reduction reactor, and a heat input device for heating the catalyst particles, according to one or more embodiments described.

FIG. 4 depicts another system for upgrading the hydrocarbon-containing feed that includes the reactor or conversion zone 1, the regenerator or combustion zone 2, the reduction reactor or reduction zone 3, and a heat input device 4 for heating the catalyst particles, according to one or more embodiments. Depending, at least in part, on the particular hydrocarbon-containing feed, catalyst particle to hydrocarbon containing feed weight ratio, the temperature of the regenerated and reduced catalyst particles, and other process variables, it can be desirable to heat at least a portion of the catalyst particles once introduced into the reactor 1. As such, in some embodiments, at least a portion of the catalyst particles within the reactor 1 can be directed via line 54 into the heat input device 4 where the catalyst particles can be heated. Any suitable heat source can be used to heat the catalyst particles. In some embodiments, heat can be indirectly transferred from a heated medium to increase the temperature of the catalyst particles to a desired temperature. Suitable heated mediums can be or can include, but are not limited to, steam, flue gas, hot oil, molten salt, and the like. In some embodiments, heat can be produced from one or more electric heating elements. The heated catalyst particles can be recovered via line 55 from the heat input device 4 and reintroduced into the reactor 1. In an alternative embodiment, the heat input device can be disposed within the reactor 1 such that the catalyst particles do not need to be removed via line 54 from the reactor 1 and returned via line 55 to the reactor 1.

Figure 5:
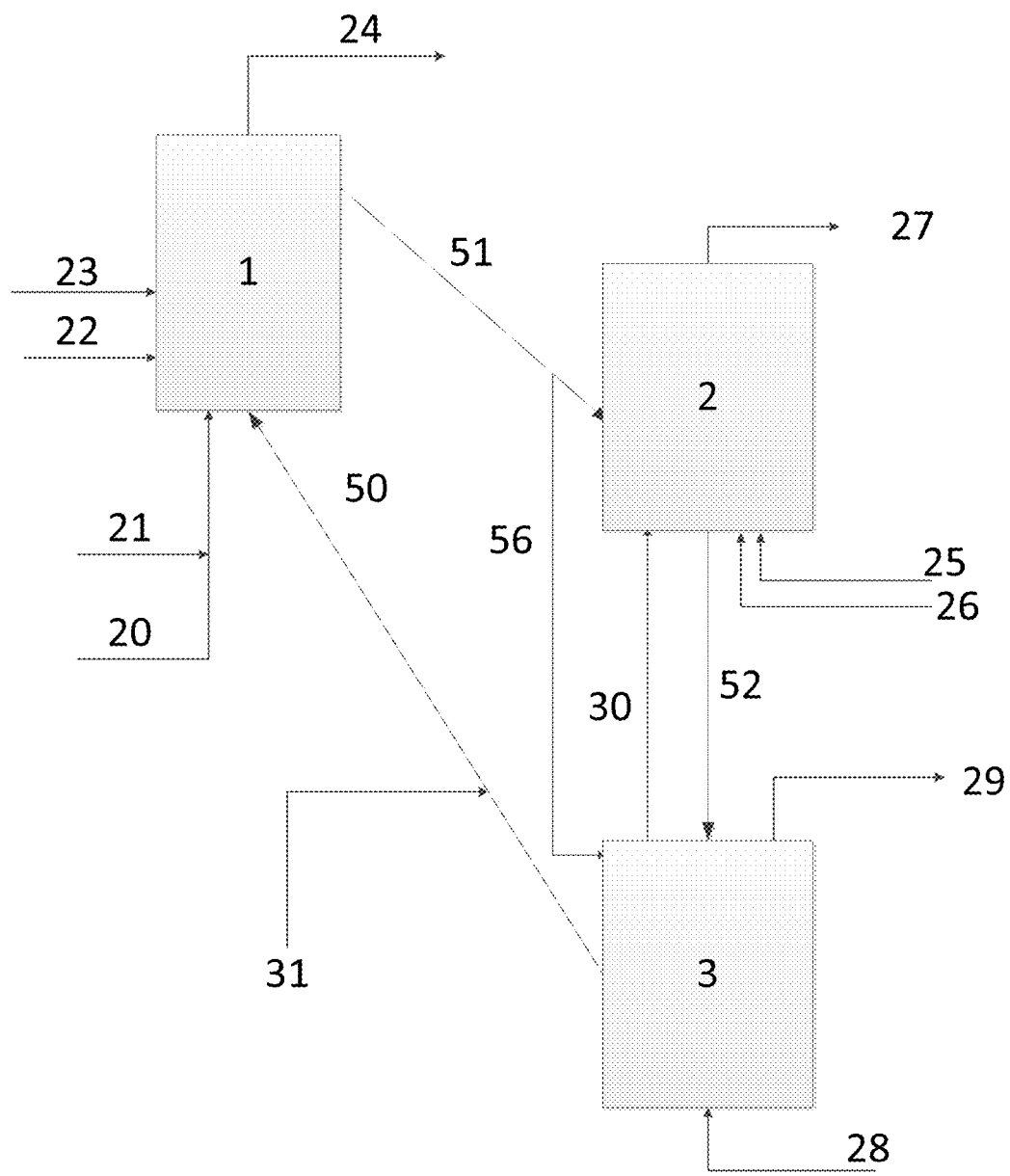
FIG. 5 depicts another system for upgrading the hydrocarbon-containing feed that includes a reactor, regenerator, a reduction reactor, and a transfer line for feeding at least a portion of coked catalyst particles into the reduction reactor, according to one or more embodiments described.

FIG. 5 depicts another system for upgrading the hydrocarbon-containing feed in line 20 that includes the reactor or conversion zone 1, the regenerator or combustion zone 2, the reduction reactor or reduction zone 3, and a transfer line 56 for feeding at least a portion of the coked catalyst particles in line 51 into the reduction zone 3, according to one or more embodiments. In some embodiments, the extent of catalyst deactivation within the reactor 1 may not be sufficient to necessitate introducing all the coked catalyst particles into the regenerator 2. As such, feeding at least a portion of the coked catalyst particles into the reduction zone 3 can be carried out to reduce or minimize the amount of catalyst particles introduced into the regenerator. Feeding at least a portion of the coked catalyst particles into the reduction zone 3 can also be used to adjust or otherwise control a temperature of the regenerated catalyst particles fed via line 52 into the reduction zone 3. In some embodiments, at least a portion of the coked catalyst particles via line 56 can be introduced into the reduction zone 3, at least a portion of the coked catalyst particles via line 53 (FIG. 3) can be recycled to the reactor 1, and at least a portion of the coked catalyst particles via line 51 can be fed into the regeneration zone 2.

Figure 6:
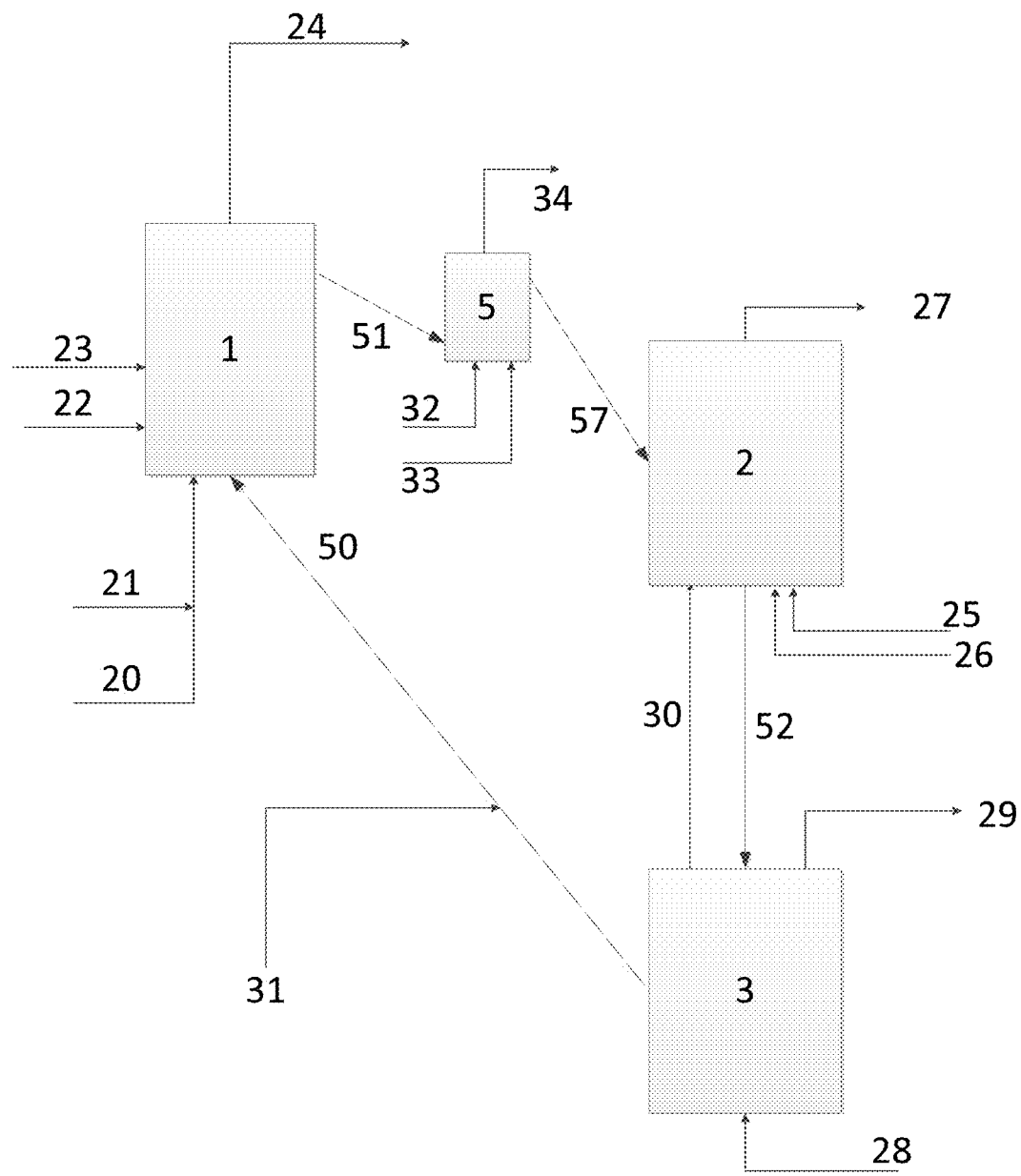
FIG. 6 depicts another system for upgrading the hydrocarbon-containing feed that includes a reactor, a regenerator, a reduction reactor, and a secondary reactor, according to one or more embodiments described.

FIG. 6 depicts another system for upgrading the hydrocarbon-containing feed in line 20 that includes the reactor or conversion zone 1, the regenerator or combustion zone 2, the reduction reactor or reduction zone 3, and a secondary reactor 5, according to one or more embodiments. The hydrocarbon-containing feed via line 20 can be introduced into the reactor 1, e.g., at a bottom end of a riser reactor or an upper end of a downer reactor. In some embodiments, a diluent gas via line 21 can be mixed with the hydrocarbon-containing feed in line 20. The hydrocarbon-containing feed and optional diluent gas can be mixed or otherwise contacted with regenerated and reduced catalyst particles introduced via line 50 into the reactor 1. The regenerated and reduced catalyst particles in line 50 can be moved or otherwise conveyed through line 50 via a transport gas introduced via line 31. As the hydrocarbon-containing feed reacts in the presence of the catalyst particles and moves through the reactor 1, additional hydrocarbon-containing feed via line 22 and/or additional diluent gas via line 23 can optionally be introduced into the reactor 1. The gaseous components and coked catalyst particles can be separated via one or more gas-solid separation devices, as previously described, with a first gaseous stream rich in the one or more upgraded hydrocarbons, unreacted hydrocarbons, molecular hydrogen, and any other gaseous components recovered via line 24 and a first particle stream rich in coked catalyst particles recovered via line 51.

The first gaseous stream via line 24 can be sent to product recovery and subjected to additional processing steps. The first particle stream rich in the coked catalyst particles can be introduced via line 51 into the secondary reactor 5. A reactant stream, e.g., additional hydrocarbon-containing feed, via line 32 and an optional diluent stream via line 33 can also be introduced into the secondary reactor 5. In some embodiments, the hydrocarbon-containing feed in line 20 can include different hydrocarbons than the reactant stream in line 32. In some embodiments, the hydrocarbon-containing feed in line 20 can require the fluidized catalyst particles be heated to a greater temperature for the desired conversion effluent to be produced than the reactant feed in line 32. As such, the upgraded hydrocarbons in line 24 and the upgraded hydrocarbons in line 34 can be the same or different with respect to one another. In another embodiment, at least part of the gaseous stream in line 24 can be introduced via line 32 into the secondary reactor 5.

The secondary product in line 34 can be separated from the coked catalyst using a gas-solid separation device, such as a cyclonic separator. The secondary product via line 34 can be sent to product recovery and subjected to additional processing steps. In another embodiment, at least part of the secondary product in line 34 can be introduced via line 20 and/or line 22 into the reactor 1. The coked catalyst particles via line 57 can be fed into the regenerator 2. The regenerator 2 can be a reactor where the coked catalyst particles can be contacted with an oxidant, e.g., air, introduced via line 25 to combust at least a portion of the coke deposited on the surface of the catalyst particles. As required, a supplemental fuel via line 26 can also be introduced into the regenerator 2. The supplemental fuel can be used to further heat the regenerated catalyst particles within the regenerator 2 to a desired temperature to support the endothermic reactions that occur within the reactor 1.

Within the regenerator 2, a gas-solid separation device can be used to separate the regenerated catalyst particles from the combustion gas with a second gaseous stream rich in the combustion gas recovered via line 27 and a second particle stream rich in the regenerated catalyst particles recovered via line 52. In some embodiments, the combustion gas in line 27, which may contain fine catalyst particulates, can be directed to a secondary separation device for recovery of fine catalyst particulates, heat recovery, or disposal.

The regenerated catalyst particles via line 52 and a reducing gas via line 28 can be introduced into the reduction reactor 3. The regenerated catalyst particles can be contacted with the reducing gas within the reduction reactor 3 to produce regenerated and reduced catalyst particles. Within the reduction reactor 3, a gas-solid separation device can be used to separate the regenerated and reduced catalyst particles from the reducing gas with a third gaseous stream rich in the reducing gas recovered via line 30 and/or line 29 and a third particle stream rich in the regenerated and reduced catalyst particles via line 50. Depending, at least in part, on the composition of the reducing gas, the reducing gas, in whole or in part, can be introduced via line 30 into the regenerator 2 to provide at least a portion of the optional supplemental fuel that can be fed into the regenerator 2. In some embodiments, the reducing gas can be removed via line 29 from the system. The regenerated and reduced catalyst particles can be introduced via line 50 into the reactor 1, with the transport gas via line 31 used to convey the catalyst particles into the reactor 1.

Figure 7:
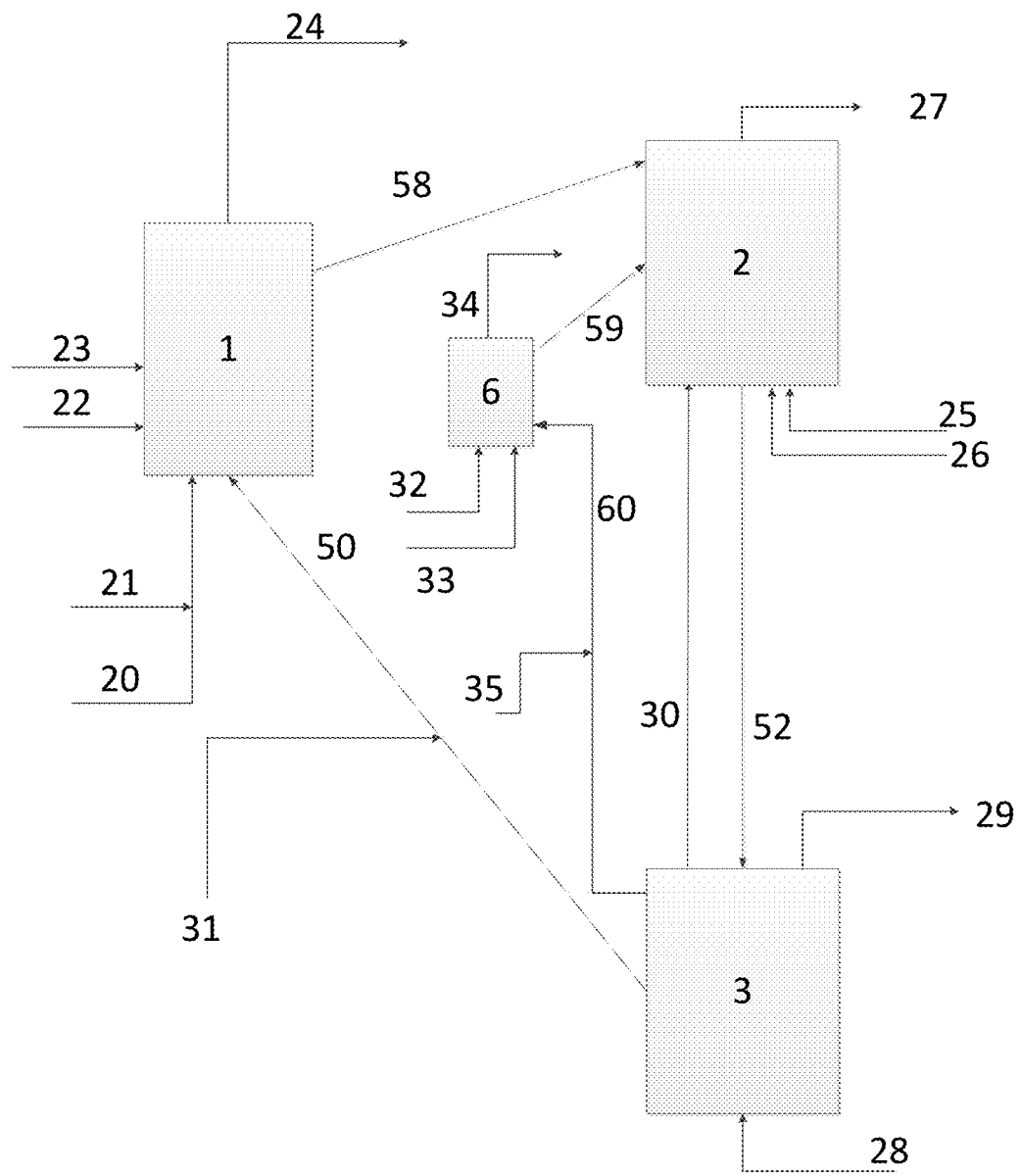
FIG. 7 depicts another system for upgrading the hydrocarbon-containing feed that includes a reactor, a regenerator, a reduction reactor, and a secondary reactor, according to one or more embodiments described.

FIG. 7 depicts another system for upgrading the hydrocarbon-containing feed in line 20 that includes the reactor or conversion zone 1, the regenerator or combustion zone 2, the reduction reactor or reduction zone 3, and a secondary reactor 6, according to one or more embodiments. The hydrocarbon-containing feed via line 20 can be introduced into the reactor 1, e.g., at a bottom end of a riser reactor or an upper end of a downer reactor. In some embodiments, a diluent gas via line 21 can be mixed with the hydrocarbon-containing feed in line 20. The hydrocarbon-containing feed and optional diluent gas can be mixed or otherwise contacted with regenerated and reduced catalyst particles introduced via line 50 into the reactor 1. The regenerated and reduced catalyst particles in line 50 can be moved or otherwise conveyed through line 50 via a transport gas introduced via line 31. As the hydrocarbon-containing feed reacts in the presence of the catalyst particles and moves through the reactor 1, additional hydrocarbon-containing feed via line 22 and/or additional diluent gas via line 23 can optionally be introduced into the reactor 1. The gaseous components and coked catalyst particles can be separated via one or more gas-solid separation devices, as previously described, with a first gaseous stream rich in the one or more upgraded hydrocarbons, unreacted hydrocarbons, molecular hydrogen, and any other gaseous components recovered via line 24 and a first particle stream rich in coked catalyst particles recovered via line 58.

The first gaseous stream via line 24 can be sent to product recovery and subjected to additional processing steps. The first particle stream rich in the coked catalyst particles can be introduced via line 58 into the regenerator 2. The regenerator 2 can be a reactor where the coked catalyst particles can be contacted with an oxidant, e.g., air, introduced via line 25 to combust at least a portion of the coke deposited on the surface of the catalyst particles. As required, a supplemental fuel via line 26 can also be introduced into the regenerator 2. The supplemental fuel can be used to further heat the regenerated catalyst particles within the regenerator 2 to a desired temperature to support the endothermic reactions that occur within the reactor 1.

Within the regenerator 2, a gas-solid separation device can be used to separate the regenerated catalyst particles from the combustion gas with a second gaseous stream rich in the combustion gas recovered via line 27 and a second particle stream rich in the regenerated catalyst particles recovered via line 52. In some embodiments, the combustion gas in line 27, which may contain fine catalyst particulates, can be directed to a secondary separation device for recovery of fine catalyst particulates, heat recovery, or disposal.

The regenerated catalyst particles via line 52 and a reducing gas via line 28 can be introduced into the reduction reactor 3. The regenerated catalyst particles can be contacted with the reducing gas within the reduction reactor 3 to produce regenerated and reduced catalyst particles. Within the reduction reactor 3, a gas-solid separation device can be used to separate the regenerated and reduced catalyst particles from the reducing gas with a third gaseous stream rich in the reducing gas recovered via line 30 and/or line 29, a third particle stream rich in the regenerated and reduced catalyst particles via line 50, and a fourth particle stream rich in the regenerated and reduced catalyst particles via line 60. Depending, at least in part, on the composition of the reducing gas, the reducing gas, in whole or in part, can be introduced via line 30 into the regenerator 2 to provide at least a portion of the optional supplemental fuel that can be fed into the regenerator 2. In some embodiments, the reducing gas can be removed via line 29 from the system.

A first portion of the regenerated and reduced catalyst particles can be introduced via line 50 into the reactor 1, with the transport gas via line 31 used to convey the catalyst particles into the reactor 1. A second portion of the regenerated and reduced catalyst particles can be introduced via line 60 into the secondary reactor 6, with a transport gas in line 35 used to convey the catalyst particles into the secondary reactor 6. A hydrocarbon-containing feed via line 32 and an optional diluent stream via line 33 can also be fed into the secondary reactor. The hydrocarbon-containing feed can contact the reduced and regenerated catalyst particles within the secondary reactor 6 to produce another conversion effluent.

The gaseous components and coked catalyst particles can be separated via one or more gas-solid separation devices, as previously described, with a second gaseous stream rich in one or more upgraded hydrocarbons, unreacted hydrocarbons, molecular hydrogen, and any other gaseous components recovered via line 34 and a particle stream rich in coked catalyst particles recovered via line 59. In another embodiment, at least part of the first gaseous stream in line 24 can be introduced via line 32 into the secondary reactor 6. In another embodiment, at least part of the second gaseous stream in line 34 can be introduced via line 20 and/or 22 into the reactor 1.

While separation of the various gaseous products, e.g., the upgraded hydrocarbons and molecular hydrogen from the coked catalyst particles, the combustion gas from the regenerated catalyst particles, and the reducing gas from the regenerated and reduced catalyst particles, is shown in FIGS. 1-7 as occurring within the reactor 1, the regenerator 2, the reduction reactor 3, the secondary reactor 5, and the secondary reactor 6, such separation can also occur outside of any one or more of those reactors.

EXAMPLES

The foregoing discussion can be further described with reference to the following non-limiting examples.

The following process steps were performed on the catalysts used in most examples below. All experiments were carried out at ambient pressure, except for the few exceptions as noted in the examples below.

1. A gas that included 10 vol % of $O_2$ in He, or air was passed through the catalyst at a regeneration temperature ($T_{regen}$) for a certain period of time ($t_{regen}$) to regenerate the catalyst.
2. Without changing the flow of the gas, the temperature within the reactor was changed from $T_{regen}$ to a reduction temperature ($T_{red}$).
3. The system was flushed with He gas.
4. A gas that included 10 vol % $H_2$ in Ar was passed through the catalyst at the $T_{red}$ for a certain period of time ($t_{red}$).
5. The system was flushed with He gas.
6. The temperature within the reactor from was changed from $T_{red}$ to a reaction temperature ($T_{rxn}$) in the presence of the inert gas.
7. A hydrocarbon-containing feed that included 90 vol % of $C_3H_8$ in Ar or Kr or He at a flow rate ($F_{rxn}$) was passed through the catalyst at the $T_{rxn}$ for a certain period of time ($t_{rxn}$). In some examples, the hydrocarbon-containing feed was passed through a sparger immersed in deionized water kept at a temperature of $T_1$, and then through a reflux with a carefully controlled temperature of $T_2$ before it was introduced into the reactor and reached the catalyst. When the sparger was used, the hydrocarbon-containing feed included a certain amount of steam within the reactor, which is shown in the relevant tables below.
8. The system was flushed with He gas.
9. The gas that included 10 vol % of $O_2$ in He, or air was again passed through the catalyst at $T_{rxn}$, and the temperature within the reactor was changed from $T_{rxn}$ to $T_{regen}$.

In certain examples, the catalyst reduction step was not carried out and the following steps were performed.

1. The gas that included 10 vol % of $O_2$ in He or air was passed through the catalyst at the $T_{regen}$ for the $t_{regen}$.
2. Without changing the flow of the gas, the temperature within the reactor was changed from $T_{regen}$ to $T_{rxn}$.
3. The system was flushed with the inert gas (such as He).
4. The hydrocarbon-containing feed that included 90 vol % of $C_3H_8$ in Ar or Kr or He at a flow rate of $F_{rxn}$ was passed through the catalyst at the $T_{rxn}$ for the $t_{rxn}$. In some examples, the hydrocarbon-containing feed was passed through the sparger immersed in deionized water kept at the temperature of $T_1$, and then through a reflux with carefully controlled temperature of T2 before it was introduced into the reactor and reached the catalyst.
5. The system was flushed with an inert gas (such as He).
6. The gas that included 10 vol % of $O_2$ in He or air was again passed through the catalyst at $T_{rxn}$, and the temperature within the reactor was changed from $T_{rxn}$ to $T_{regen}$.

An AGILENT® microGC 490 was used to measure the composition of the reactor effluent every 1 minute to 1.5 minutes. The concentration of each component in the reactor effluent was then used to calculate the $C_3H_6$ yield and selectivity. The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in the data tables below. For some experiments, repeated cycles were conducted to understand catalyst stability. The $C_3H_6$ yield as reported in these examples are based on carbon only.

In each example, a certain amount of the catalyst $M_{cat}$ was mixed with an appropriate amount of quartz/SiC diluent and loaded in a quartz reactor. The amount of diluent is determined so that the catalyst bed (catalyst+diluent) is largely isothermal during operation. The dead volume of the reactor was filled with quartz chips/rods.

When the reaction temperature ($T_{rxn}$) was >620° C., thermal cracking of propane/propylene became significant. Since thermal cracking of propane/propylene has a much higher selectivity to $C_1$ and $C_2$ hydrocarbons, the overall selectivity to $C_3H_6$ is reduced. The amount of thermal cracking within the reactor is related to how much quartz/SiC diluent was added into the reactor and how well the dead volume within the reactor was reduced by the packing materials. Therefore, depending on how the reactor is packed in different experiments, the performance varies. As such, the experimental results shown in different tables are not necessarily comparable to one another.

Examples 1-23, Catalyst 1

Catalyst 1: The catalyst used in Examples 1-23 (Exs. 1-23) was a Pt-based, Sn-containing catalyst supported on an Mg/Al mixed oxide support, crushed and sieved to 20-40 mesh particle size. Elemental analysis showed that the catalyst contained 0.48 wt % of Pt, 1.25 wt % of Sn, 67.93 wt % of Mg, and 29.23 wt % of Al, based on the total weight of the metal elements, with an Mg to Al molar ratio of about 2.58.

Figure 8:
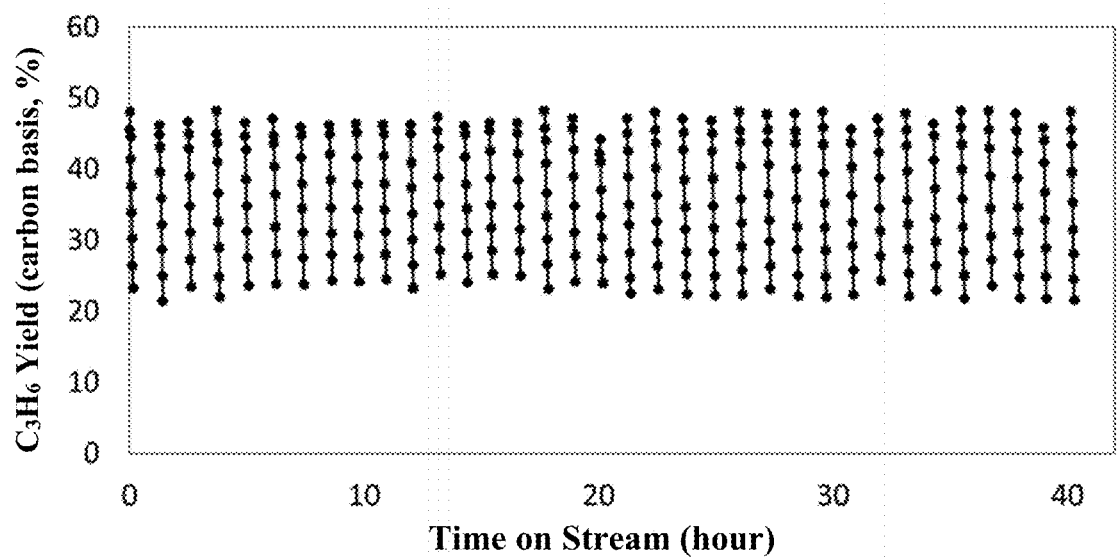
FIG. 8 shows the catalyst stability results of a catalyst used in Examples 1-3 after having undergone 35 cycles (regeneration, reduction, and dehydrogenation) carried out under the same conditions used in Example 1.

Table 1 shows the experimental results for Examples 1-3. A comparison between Ex. 1 and Ex. 3 shows that the reduction of the catalyst in the presence of molecular hydrogen after the oxidative regeneration improve the propylene yield. Ex. 1 and Ex. 3 also show that the catalyst is not very sensitive to the duration of the reduction step (1 minute vs. 5 minutes) under the experimental conditions used for these examples. At other conditions, however, there might be an optimal duration for the reduction step to be carried out. FIG. 8 shows the catalyst stability results of the catalyst used in Examples 1-3 after having undergone 35 cycles (regeneration, reduction, and dehydrogenation) carried out under the same conditions used in Example 1. Table 2 shows the experimental results for Examples 4 and 5. The results in Table 2 show that the reduction step can be carried out at different temperatures (670° C. versus 750° C.).

TABLE 1

| | | Ex. 1 | Ex. 2 | Ex. 3 |
|---|---|---|---|---|
| Catalyst | | 1 | 1 | 1 |
| $M_{cat}$ (g) | | 1 | 1 | 1 |
| $T_{rxn}$ (° C.) | | 620 | 620 | 620 |
| $t_{rxn}$ (min) | | 10 | 10 | 10 |
| $F_{rxn}$ (sccm) | | 22 | 22 | 22 |
| $S_{vol}$ (%) | | NA | NA | NA |
| $T_{red}$ (° C.) | | 620 | NA | 620 |
| $t_{red}$ (min) | | 1 | NA | 5 |
| $T_{regen}$ (° C.) | | 620 | 620 | 620 |
| $t_{regen}$ (min) | | 30 | 30 | 30 |
| Cycles | | 35 | 1 | 1 |
| First cycle | $Y_{ini}$ | 48.1 | 21.2 | 48.2 |
| | $Y_{end}$ | 23.2 | 6.8 | 24 |
| | $S_{ini}$ | 98 | 96.4 | 98 |
| | $S_{end}$ | 93.8 | 89.6 | 93.7 |

TABLE 2

| | | Ex. 4 | Ex. 5 |
|---|---|---|---|
| Catalyst | | 1 | 1 |
| $M_{cat}$ (g) | | 0.773 | 0.773 |
| $T_{rxn}$ (° C.) | | 670 | 670 |
| $t_{rxn}$ (min) | | 10 | 10 |
| $F_{rxn}$ (sccm) | | 17 | 17 |
| $S_{vol}$ (vol %) | | 11 | 11 |
| $T_{red}$ (° C.) | | 670 | 750 |
| $t_{red}$ (min) | | 1 | 1 |
| $T_{regen}$ (° C.) | | 800 | 800 |
| $t_{regen}$ (min) | | 30 | 30 |
| Cycles | | 1 | 1 |
| First cycle | $Y_{ini}$ | 63.1 | 61.9 |
| | $Y_{end}$ | 61.7 | 61 |
| | $S_{ini}$ | 86.7 | 87.7 |
| | $S_{end}$ | 87.9 | 88.3 |

Table 3 shows the experimental results for Examples 6-10. Examples 6-10 were conducted by introducing a partial plug at the exhaust of the reactor so that as the hydrocarbon-containing feed passed through the reactor at room temperature, e.g., 25° C., the pressure indicator upstream of the reactor read 1.43 bara. During the experiment, the gas volumetric flow rate in the reactor was expected to increase due to steam addition, higher T and volume expansion of the flow due to propane dehydrogenation. Therefore, the pressure within the reactor should have been significantly higher than 1.43 bara. Unfortunately, the pressure during reactor could not be monitored due to equipment limitations. Experiments 8-10 show the effect of conducting the regeneration at different temperatures and durations.

TABLE 3

| | | Ex. 6 | Ex. 7 | Ex. 8 | Ex. 9 | Ex. 10 |
|---|---|---|---|---|---|---|
| P (bara) | | 1.43 | 1.43 | 1.43 | 1.43 | 1.43 |
| Catalyst | | 1 | 1 | 1 | 1 | 1 |
| $M_{cat}$ (g) | | 0.773 | 0.773 | 0.773 | 0.773 | 0.773 |
| $T_{rxn}$ (° C.) | | 670 | 660 | 680 | 670 | 670 |
| $t_{rxn}$ (min) | | 10 | 10 | 10 | 10 | 10 |
| $F_{rxn}$ (sccm) | | 34 | 34 | 34 | 34 | 34 |
| $S_{vol}$ (vol %) | | 11 | 11 | 11 | 11 | 11 |
| $T_{red}$ (° C.) | | 670 | 660 | 680 | 670 | 670 |
| $t_{red}$ (min) | | 1 | 1 | 1 | 1 | 1 |
| $T_{regen}$ (° C.) | | 800 | 800 | 800 | 800 | 900 |
| $t_{regen}$ (min) | | 30 | 30 | 30 | 45 | 30 |
| Cycles | | 8 | 8 | 1 | 7 | 7 |
| First cycle | $Y_{ini}$ | 57.9 | 56.2 | 58.1 | 58.4 | 57.3 |
| | $Y_{end}$ | 55.9 | 53.9 | 55.2 | 56.7 | 54.1 |
| | $S_{ini}$ | 89 | 91 | 86.2 | 89 | 88.9 |
| | $S_{end}$ | 89.6 | 91.7 | 87 | 89.7 | 89.5 |
| Last cycle | $Y_{ini}$ | 57.5 | 56.2 | NA | 58.5 | NA |
| | $Y_{end}$ | 55.4 | 54.2 | NA | 57.1 | NA |
| | $S_{ini}$ | 88.9 | 91 | NA | 88.9 | NA |
| | $S_{end}$ | 89.7 | 91.7 | NA | 89.7 | NA |

Table 4 shows the experimental results for Examples 11-14. The result sin Table 4 shown the effect space velocity had on the performance of the catalyst. Table 5 shows the experimental results of Examples 15 and 16. Table 5 shows the effect of reduction in the presence of steam, respectively. Table 6 shows the results of Examples 17 and 18. Table 6 shows the effect of regeneration duration.

TABLE 4

| | | Ex. 11 | Ex. 12 | Ex. 13 | Ex. 14 |
|---|---|---|---|---|---|
| Catalyst | | 1 | 1 | 1 | 1 |
| $M_{cat}$ (g) | | 0.193 | 0.193 | 0.193 | 0.193 |
| $T_{rxn}$ (° C.) | | 670 | 670 | 670 | 700 |
| $t_{rxn}$ (min) | | 10 | 10 | 10 | 10 |
| $F_{rxn}$ (sccm) | | 34 | 17 | 9 | 17 |
| $S_{vol}$ (vol %) | | 11 | 11 | 11 | 11 |
| $T_{red}$ (° C.) | | 670 | 670 | 670 | 670 |
| $t_{red}$ (min) | | 1 | 1 | 1 | 1 |
| $T_{regen}$ (° C.) | | 800 | 800 | 800 | 800 |
| $t_{regen}$ (min) | | 30 | 30 | 30 | 30 |
| Cycles | | 1 | 1 | 1 | 1 |
| First cycle | $Y_{ini}$ | 54.1 | 59.3 | 60.6 | 58.5 |
| | $Y_{end}$ | 45 | 51.9 | 56 | 44.4 |
| | $S_{ini}$ | 95.2 | 92.8 | 89.6 | 86.3 |
| | $S_{end}$ | 94.4 | 92.3 | 89.3 | 82.8 |

TABLE 5

| | Ex. 15 | Ex. 16 |
|---|---|---|
| Catalyst | 1 | 1 |
| $M_{cat}$ (g) | 0.193 | 0.193 |
| $T_{rxn}$ (° C.) | 670 | 670 |
| $t_{rxn}$ (min) | 10 | 10 |
| $F_{rxn}$ (sccm) | 9 | 9 |
| $S_{vol}$ (vol %) | 11 | 11 |
| $T_{red}$ (° C.) | 670 | NA |
| $t_{red}$ (min) | 1 | NA |
| $T_{regen}$ (° C.) | 800 | 800 |

TABLE 5-continued

|  |  | Ex. 15 | Ex. 16 |
|---|---|---|---|
| $t_{regen}$ (min) |  | 30 | 30 |
| Cycles |  | 1 | 1 |
| First cycle | $Y_{ini}$ | 58.4 | 22.4 |
|  | $Y_{end}$ | 50.2 | 13.7 |
|  | $S_{ini}$ | 90.2 | 79.4 |
|  | $S_{end}$ | 89.7 | 68.7 |

TABLE 6

|  |  | Ex. 17 | Ex. 18 |
|---|---|---|---|
| Catalyst |  | 1 | 1 |
| $M_{cat}$ (g) |  | 0.773 | 0.773 |
| $T_{rxn}$ (° C.) |  | 670 | 670 |
| $t_{rxn}$ (min) |  | 10 | 10 |
| $F_{rxn}$ (sccm) |  | 17 | 17 |
| $S_{vol}$ (vol %) |  | 11 | 11 |
| $T_{red}$ (° C.) |  | 670 | 670 |
| $t_{red}$ (min) |  | 1 | 1 |
| $T_{regen}$ (° C.) |  | 800 | 800 |
| $t_{regen}$ (min) |  | 30 | 10 |
| Cycles |  | 1 | 1 |
| First cycle | $Y_{ini}$ | 58.2 | 56.7 |
|  | $Y_{end}$ | 55.1 | 51.7 |
|  | $S_{ini}$ | 89.5 | 89.7 |
|  | $S_{end}$ | 89 | 89.1 |

Figure 9:
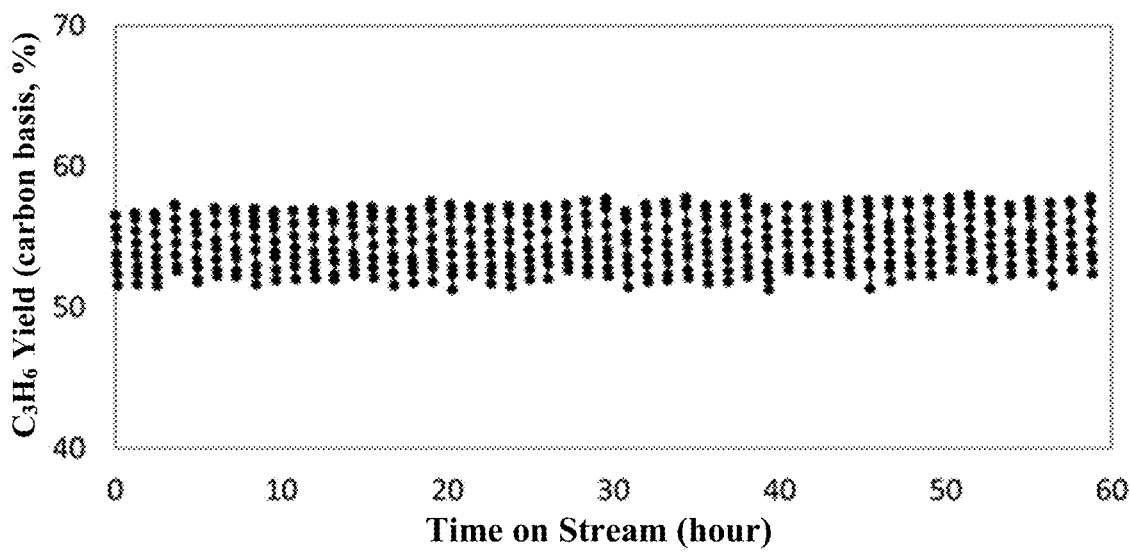
FIG. 9 shows the catalyst stability results of the catalyst used in Example 23 after having undergone 49 cycles (regeneration, reduction, and dehydrogenation) in the presence of steam.

Table 7 shows the results of Examples 19-22. Table 7 shows the effect the amount steam in the hydrocarbon-containing feed has on the yield and selectivity. In Ex. 23, the catalyst was subjected to 49 cycles total in the presence of about 11 vol % steam. The results of Ex. 23 are shown in Table 8. FIG. 9 shows the catalyst stability results of the catalyst used in Example 23 after having undergone 49 cycles (regeneration, reduction, and dehydrogenation) in the presence of steam.

TABLE 7

|  |  | Ex. 19 | Ex. 20 | Ex. 21 | Ex. 22 |
|---|---|---|---|---|---|
| Catalyst |  | 1 | 1 | 1 | 1 |
| $M_{cat}$ (g) |  | 0.773 | 0.773 | 0.773 | 0.773 |
| $T_{rxn}$ (° C.) |  | 670 | 670 | 650 | 650 |
| $t_{rxn}$ (min) |  | 10 | 10 | 10 | 10 |
| $F_{rxn}$ (sccm) |  | 17 | 17 | 17 | 17 |
| $S_{vol}$ (vol %) |  | 3 | 11 | 11 | NA |
| $T_{red}$ (° C.) |  | 670 | 670 | 650 | 650 |
| $t_{red}$ (min) |  | 1 | 1 | 1 | 1 |
| $T_{regen}$ (° C.) |  | 670 | 670 | 650 | 650 |
| $t_{regen}$ (min) |  | 30 | 30 | 30 | 30 |
| Cycles |  | 1 | 1 | 1 | 1 |
| First cycle | $Y_{ini}$ | 54.9 | 58.5 | 56.8 | 52.1 |
|  | $Y_{end}$ | 49.9 | 55.4 | 55.3 | 22 |
|  | $S_{ini}$ | 90.7 | 90.4 | 93.6 | 90.8 |
|  | $S_{end}$ | 88.8 | 90 | 93.6 | 84.7 |

TABLE 8

|  |  | Ex. 23 |
|---|---|---|
| Catalyst |  | 1 |
| $M_{cat}$ (g) |  | 0.773 |
| $T_{rxn}$ (° C.) |  | 670 |
| $t_{rxn}$ (min) |  | 10 |
| $F_{rxn}$ (sccm) |  | 17 |
| $S_{vol}$ (vol %) |  | 11 |
| $T_{red}$ (° C.) |  | 670 |
| $t_{red}$ (min) |  | 1 |
| $T_{regen}$ (° C.) |  | 670 |

TABLE 8-continued

|  |  | Ex. 23 |
|---|---|---|
| $t_{regen}$ (min) |  | 30 |
| Cycles |  | 49 |
| First cycle | $Y_{ini}$ | 56.5 |
|  | $Y_{end}$ | 51.6 |
|  | $S_{ini}$ | 89.8 |
|  | $S_{end}$ | 89 |
| Last cycle | $Y_{ini}$ | 57.6 |
|  | $Y_{end}$ | 52.4 |
|  | $S_{ini}$ | 89.8 |
|  | $S_{end}$ | 88.8 |

Example 24, Catalyst 2

The catalyst included 1 wt % of Pt and 3 wt % of Sn supported on CeO2, based on the weight of the CeO2. The CeO2 support was made by calcining cerium (III) nitrate hexahydrate (Sigma-Aldrich 202991). The catalyst was made by incipient wetness impregnation of 3 g of $CeO_2$ with 0.788 g of 8 wt % chloroplatinic acid in water (Sigma Aldrich, 262587) and 0.266 g of tin (IV) chloride pentahydrate (Acros Organics 22369), followed by drying and calcination at 800° C. for 12 h. The data in Table 9 shows that the catalyst was stable over 42 cycles.

Examples 25 and 26, Catalyst 3

The catalyst included 1 wt % of Pt and 2.7 wt % of Sn supported on Ceria-Zirconia, based on the weight of the Ceria-Zirconia. The Catalyst was made by incipient wetness impregnation of 16.5 g of Ceria-Zirconia (Sigma Aldrich 634174) with 0.44 g of chloroplatinic acid hexahydrate (BioXtra, P7082) and 1.33 g of tin (IV) chloride pentahydrate (Acros Organics 22369) dissolved in an appropriate amount of deionized water, followed by drying and calcination at 800° C. for 12 h. Results are shown in Table 10.

TABLE 9

|  |  | Ex. 24 |
|---|---|---|
| Catalyst |  | 2 |
| $M_{cat}$ (g) |  | 0.5 |
| $T_{rxn}$ (° C.) |  | 540 |
| $t_{rxn}$ (min) |  | 10 |
| $F_{rxn}$ (sccm) |  | 12.3 |
| $S_{vol}$ (vol %) |  | NA |
| $T_{red}$ (° C.) |  | NA |
| $t_{red}$ (min) |  | NA |
| $T_{regen}$ (° C.) |  | 540 |
| $t_{regen}$ (min) |  | 10 |
| Cycles |  | 42 |
| First cycle | $Y_{ave}$ | 15 |
|  | $S_{ave}$ | 84.3 |
| Last cycle | $Y_{ave}$ | 14.8 |
|  | $S_{ave}$ | 89.7 |

TABLE 10

|  | Ex. 25 | Ex. 26 |
|---|---|---|
| Catalyst | 3 | 3 |
| $M_{cat}$ (g) | 0.456 | 0.456 |
| $T_{rxn}$ (° C.) | 540 | 580 |
| $t_{rxn}$ (min) | 10 | 10 |
| $F_{rxn}$ (sccm) | 11 | 11 |
| $S_{vol}$ (vol %) | NA | NA |
| $T_{red}$ (° C.) | NA | NA |

TABLE 10-continued

|  |  | Ex. 25 | Ex. 26 |
|---|---|---|---|
| $t_{red}$ (min) |  | NA | NA |
| $T_{regen}$ (° C.) |  | 540 | 580 |
| $t_{regen}$ (min) |  | 10 | 10 |
| Cycles |  | 10 | 12 |
| First cycle | $Y_{ini}$ | 22.2 | 28.6 |
|  | $Y_{end}$ | 10.6 | 9.9 |
|  | $S_{ini}$ | 85.5 | 75.9 |
|  | $S_{end}$ | 91.3 | 91 |
| Last cycle | $Y_{ini}$ | 21.4 | 28.8 |
|  | $Y_{end}$ | 11.7 | 10.4 |
|  | $S_{ini}$ | 86.2 | 76.9 |
|  | $S_{end}$ | 91.3 | 91.1 |

Examples 27-29, Catalyst 4

The catalyst included 1 wt % of Pt and 2.7 wt % of Sn supported on $Y_2O_3$, based on the weight of the $Y_2O_3$. The catalyst was made by incipient wetness impregnation of 4 g of $Y_2O_3$ (US nano 3553) with 0.106 g of chloroplatinic acid hexahydrate (BioXtra, P7082) and 0.322 g of tin (IV) chloride pentahydrate (Acros Organics 22369) dissolved in an appropriate amount of deionized water, followed by drying and calcination at 800° C. for 12 h. The data in Table 11 shows the performance of the catalyst was stable over 20 cycles.

Examples 30-34, Catalyst 5

The catalyst included 1 wt % of Pt, 2.7 wt % of Sn supported on a $CeO_2$ and $Al_2O_3$ support. The $CeO_2$ and $Al_2O_3$ support was made by incipient wetness impregnation of 8.25 g of alumina (Sigma Aldrich 199443) with 5.67 g of cerium (III) nitrate hexahydrate (Sigma Aldrich 202991) dissolved in an appropriate amount of deionized water, followed by drying and calcination at 800° C. for 12 h. The catalyst was made by incipient wetness impregnation of the $CeO_2$ and $Al_2O_3$ support with 0.22 g of chloroplatinic acid hexahydrate (BioXtra, P7082) and 0.67 g of tin (IV) chloride pentahydrate (Acros Organics 22369) dissolved in an appropriate amount of deionized water, followed by drying and calcination at 800° C. for 12 h. The data in Table 12 shows that both the co-addition of steam and catalyst pre-reduction helped to increase the yield and selectivity.

TABLE 11

|  |  | Ex. 27 | Ex. 28 | Ex. 29 |
|---|---|---|---|---|
| Catalyst |  | 4 | 4 | 4 |
| $M_{cat}$ (g) |  | 0.456 | 0.456 | 0.456 |
| $T_{rxn}$ (° C.) |  | 540 | 540 | 540 |
| $t_{rxn}$ (min) |  | 10 | 10 | 10 |
| $F_{rxn}$ (sccm) |  | 11 | 11 | 11 |
| $S_{vol}$ (vol %) |  | NA | NA | NA |
| $T_{red}$ (° C.) |  | NA | NA | 540 |
| $t_{red}$ (min) |  | NA | NA | 30 |
| $T_{regen}$ (° C.) |  | 540 | 540 | 540 |
| $t_{regen}$ (min) |  | 10 | 20 | 10 |
| Cycles |  | 20 | 1 | 1 |
| First cycle | $Y_{ini}$ | 22.7 | 23.2 | 23.9 |
|  | $Y_{end}$ | 14.9 | 16 | 17.1 |
|  | $S_{ini}$ | 89.5 | 89.3 | 92.3 |
|  | $S_{end}$ | 94 | 94 | 94.8 |
| Last cycle | $Y_{ini}$ | 23.3 | NA | NA |
|  | $Y_{end}$ | 16.2 | NA | NA |
|  | $S_{ini}$ | 90.5 | NA | NA |
|  | $S_{end}$ | 94 | NA | NA |

TABLE 12

|  |  | Ex. 31 | Ex. 32 | Ex. 33 | Ex. 34 |
|---|---|---|---|---|---|
| Catalyst |  | 5 | 5 | 5 | 5 |
| $M_{cat}$ (g) |  | 0.228 | 0.228 | 0.228 | 0.228 |
| $T_{rxn}$ (° C.) |  | 620 | 620 | 620 | 620 |
| $t_{rxn}$ (min) |  | 10 | 10 | 10 | 10 |
| $F_{rxn}$ (sccm) |  | 17 | 17 | 17 | 17 |
| $S_{vol}$ (vol %) |  | NA | 11 | NA | 11 |
| $T_{red}$ (° C.) |  | 620 | NA | NA | 620 |
| $t_{red}$ (min) |  | 1 | NA | NA | 1 |
| $T_{regen}$ (° C.) |  | 620 | 620 | 620 | 620 |
| $t_{regen}$ (min) |  | 10 | 10 | 10 | 10 |
| Cycles |  | 1 | 1 | 1 | 1 |
| First cycle | $Y_{ini}$ | 27.8 | 25.8 | 9.2 | 33.5 |
|  | $Y_{end}$ | 24.6 | 20.9 | 3.1 | 29.2 |
|  | $S_{ini}$ | 91.5 | 90.9 | 89.3 | 92 |
|  | $S_{end}$ | 92.3 | 92.3 | 81.6 | 92.7 |

Examples 35-38, Catalyst 6

The catalyst was 0.2 wt % of Pt, 0.2 wt % of Sn, and 0.67 wt % of K on high surface area $ZrO_2$ obtained from Alfa Aesar. The data in Table 13 shows that the catalyst was stable over 24 cycles and that the addition of steam significantly enhanced the yield.

TABLE 13

|  |  | Ex. 35 | Es. 36 | Ex. 37 | Ex. 38 |
|---|---|---|---|---|---|
| Catalyst |  | 6 | 6 | 6 | 6 |
| $M_{cat}$ (g) |  | 0.57 | 0.57 | 0.57 | 0.57 |
| $T_{rxn}$ (° C.) |  | 620 | 620 | 620 | 620 |
| $t_{rxn}$ (min) |  | 10 | 10 | 10 | 10 |
| $F_{rxn}$ (sccm) |  | 10 | 10 | 10 | 10 |
| $S_{vol}$ (vol %) |  | 11 | NA | NA | 1 |
| $T_{red}$ (° C.) |  | 620 | NA | 620 | 620 |
| $t_{red}$ (min) |  | 1 | NA | 1 | 1 |
| $T_{regen}$ (° C.) |  | 800 | 620 | 620 | 620 |
| $t_{regen}$ (min) |  | 30 | 30 | 30 | 30 |
| Cycles |  | 24 | 1 | 1 | 1 |
| First cycle | $Y_{ini}$ | 25.7 | 7 | 8.3 | 30.6 |
|  | $Y_{end}$ | 19.4 | 6.5 | 6.8 | 25.1 |
|  | $S_{ini}$ | 78.9 | 90.4 | 90.2 | 85.7 |
|  | $S_{end}$ | 78.4 | 90.6 | 90.2 | 84.2 |
| Last cycle | $Y_{ini}$ | 24.7 | NA | NA | NA |
|  | $Y_{end}$ | 19.5 | NA | NA | NA |
|  | $S_{ini}$ | 80.7 | NA | NA | NA |
|  | $S_{end}$ | 80.2 | NA | NA | NA |

Catalyst Compositions 7-20

Catalyst Compositions 7-20 were prepared according to the following procedure. For each catalyst composition PURALOX® MG 80/150 (3 grams) (Sasol), which was a mixed Mg/Al metal oxide that contained 80 wt % of MgO and 20 wt % of $Al_2O_3$ and had a surface area of 150 m²/g, was calcined under air at 550° C. for 3 hours to form a support. Solutions that contained a proper amount of tin (IV) chloride pentahydrate when used to make the catalyst composition (Acros Organics) and/or chloroplatinic acid when used to make the catalyst composition (Sigma Aldrich), and 1.8 ml of deionized water were prepared in small glass vials. The calcined PURALOX® MG 80/150 supports (2.3 grams) for each catalyst composition were impregnated with the corresponding solution. The impregnated materials were allowed to equilibrate in a closed container at room temperature (RT) for 24 hours, dried at 110° C. for 6 hours, and calcined at 800° C. for 12 hours.

Table 14 shows the nominal Pt and Sn content of each catalyst composition based on the weight of the support.

TABLE 14

| Catalyst | Pt (wt %) | Sn (wt %) |
|---|---|---|
| 7 | 0.4 | 1 |
| 8 | 0.3 | 1 |
| 9 | 0.2 | 1 |
| 10 | 0.1 | 1 |
| 11 | 0.05 | 1 |
| 12 | 0.025 | 1 |
| 13 | 0.0125 | 1 |
| 14 | 0 | 1 |
| 15 | 0.1 | 0.5 |
| 16 | 0.1 | 1 |
| 17 | 0.1 | 2 |
| 18 | 0.0125 | 0 |
| 19 | 0.0125 | 0.5 |
| 20 | 0.0125 | 2 |

Examples Using the Catalyst Compositions of Examples 7-20

Fixed bed experiments were conducted at approximately 100 kPa-absolute that used catalysts 7-14. A gas chromatograph (GC) was used to measure the composition of the reactor effluents. The concentrations of each component in the reactor effluents were then used to calculate the $C_3H_6$ yield and selectivity. The $C_3H_6$ yield and selectivity, as reported in these examples, were calculated on the carbon mole basis.

In each example, 0.3 g of the catalyst composition was mixed with an appropriate amount of quartz diluent and loaded into a quartz reactor. The amount of diluent was determined so that the catalyst bed (catalyst+diluent) overlapped with the isothermal zone of the quartz reactor and the catalyst bed was largely isothermal during operation. The dead volume of the reactor was filled with quartz chips/rods.

The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in Tables 5 and 6 below for catalysts 7-14.

The process steps for catalysts 7-14 were as follows: 1. The system was flushed with an inert gas. 2. Dry air at a flow rate of 83.9 sccm was passed through a by-pass of the reaction zone, while an inert gas was passed through the reaction zone. The reaction zone was heated to a regeneration temperature of 800° C. 3. Dry air at a flow rate of 83.9 sccm was then passed through the reaction zone for 10 min to regenerate the catalyst. 4. The system was flushed with an inert gas. 5. A $H_2$ containing gas with 10 vol % $H_2$ and 90 vol % Ar at a flow rate of 46.6 sccm was passed through the by-pass of the reaction zone for a certain period of time, while an inert gas was passed through the reaction zone. This is then followed by flowing the $H_2$ containing gas through the reaction zone at 800° C. for 3 seconds. 6. The system was flushed with an inert gas. During this process, the temperature of the reaction zone was changed from 800° C. to a reaction temperature of 670° C. 7. A hydrocarbon-containing (HCgas) feed that included 81 vol % of $C_3H_8$, 9 vol % of inert gas (Ar or Kr) and 10 vol % of steam at a flow rate of 35.2 sccm was passed through the by-pass of the reaction zone for a certain period of time, while an inert gas was passed through the reaction zone. The hydrocarbon-containing feed was then passed through the reaction zone at 670° C. for 10 min. GC sampling of the reaction effluent started as soon as the feed was switched from the by-pass of the reaction zone to the reaction zone.

The above process steps were repeated in cycles until stable performance was obtained. Tables 15 and 16 show that Catalyst 12 that contained only 0.025 wt % of Pt and 1 wt % of Sn had both a similar yield and a similar selectivity as compared to Catalyst 7 that contained 0.4 wt % of Pt and 1 wt % of Sn, which was surprising and unexpected. Catalyst 14 that did not include any Pt did not show an appreciable propylene yield.

TABLE 15

| | | Catalyst 7 | Catalyst 8 | Catalyst 9 | Catalyst 10 |
|---|---|---|---|---|---|
| Performance | $Y_{ini}$ | 61.7 | 61.7 | 60.7 | 63.7 |
| | $Y_{end}$ | 55.2 | 55.7 | 54.2 | 56.7 |
| | $S_{ini}$ | 97.3 | 97.2 | 97.0 | 97.1 |
| | $S_{end}$ | 98.1 | 98.0 | 97.7 | 98.3 |

TABLE 16

| | | Catalyst 11 | Catalyst 12 | Catalyst 13 | Catalyst 14 |
|---|---|---|---|---|---|
| Performance | $Y_{ini}$ | 62.4 | 62.0 | 56.7 | 2.0 |
| | $Y_{end}$ | 57.2 | 54.6 | 45.7 | 1.7 |
| | $S_{ini}$ | 96.7 | 97.3 | 96.9 | 64.2 |
| | $S_{end}$ | 97.7 | 98.0 | 97.6 | 49.5 |

Catalyst compositions 15-20 were also tested using the same process steps 1-7 described above with regard to catalysts 7-14. Table 17 shows that the level of Sn should not be too low or too high for optimal propylene yield for the catalyst compositions that included 0.1 wt % of Pt based on the weight of the support.

TABLE 17

| | | Catalyst 15 0.5 wt % Sn | Catalyst 10 1 wt % Sn | Catalyst 16 1 wt % Sn | Catalyst 17 2 wt % Sn |
|---|---|---|---|---|---|
| Performance | $Y_{ini}$ | 58.4 | 63.7 | 63.4 | 56.5 |
| | $Y_{end}$ | 49.5 | 56.7 | 55.5 | 47.7 |
| | $S_{ini}$ | 96.9 | 97.1 | 97.2 | 97.8 |
| | $S_{end}$ | 97.6 | 98.3 | 98.1 | 98.2 |

Table 18 shows that the level of Sn should not be too high or too low for optimal propylene yield for the catalyst compositions that included 0.0125 wt % of Pt based on the weight of the support.

TABLE 18

| | | Catalyst 18 0 wt % Sn | Catalyst 19 0.5 wt % Sn | Catalyst 13 1 wt % Sn | Catalyst 20 2 wt % Sn |
|---|---|---|---|---|---|
| Performance | $Y_{ini}$ | 2.6 | 44 | 56.7 | 55.4 |
| | $Y_{end}$ | 1.7 | 24.4 | 45.7 | 44.1 |
| | $S_{ini}$ | 63.9 | 96.7 | 96.9 | 96.8 |
| | $S_{end}$ | 61.1 | 95.6 | 97.6 | 97.6 |

Figure 10:
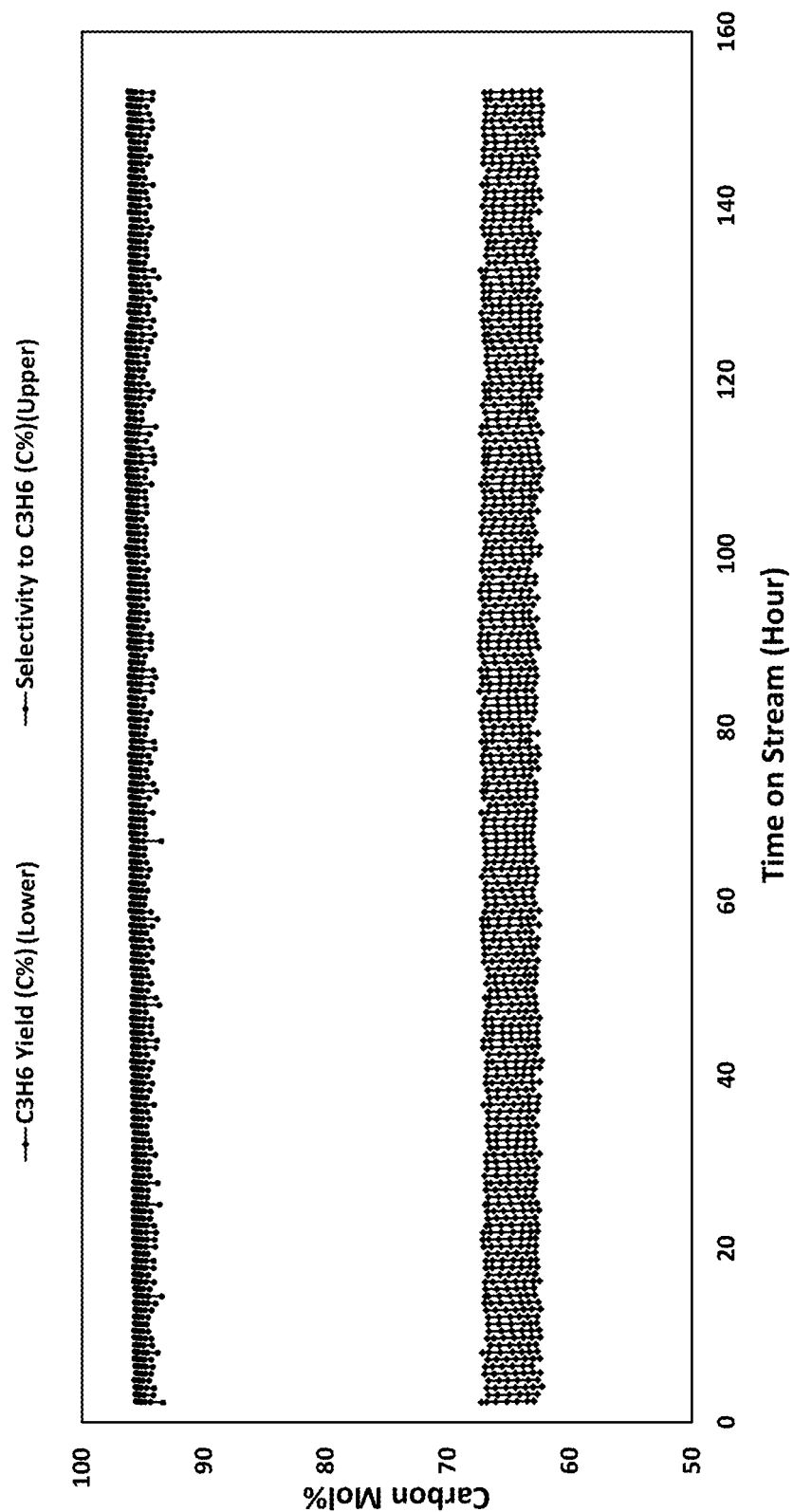
FIG. 10 shows a catalyst composition (catalyst 12) maintained its performance for 204 cycles.

Catalyst composition 12 that contained only 0.025 wt % of Pt and 1 wt % of Sn was also subjected to a longevity test using the same process steps 1-7 described above with regard to catalysts 7 to 14, except a flow rate of 17.6 sccm was used instead of 35.2 sccm in step 7. FIG. 10 shows that catalyst composition 12 maintained performance for 204 cycles (x-axis is time, y-axis is $C_3H_6$ yield and selectivity to $C_3H_6$, both in carbon mole %).

This disclosure can further include the following non-limiting embodiments/aspects:

E1. A process for upgrading a hydrocarbon, comprising:
(I) contacting a hydrocarbon-containing feed with fluidized catalyst particles comprising a Group 8-10 element disposed on a support within a conversion zone to effect one or more of dehydrogenation, dehydroaromatization, and dehydrocyclization of at least a portion of the hydrocarbon-containing feed to produce a conversion effluent comprising coked catalyst particles, one or more upgraded hydrocarbons, and molecular hydrogen, wherein: the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof; the hydrocarbon-containing feed and catalyst particles are contacted at a temperature in a range from 300° C. to 900° C., for a time period in a range from 0.1 seconds to 2 minutes, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the hydrocarbon-containing feed; the catalyst particles comprise from 0.001 wt % to 6 wt % of the Group 8-10 element based on the weight of the support; and the one or more upgraded hydrocarbons comprise a dehydrogenated hydrocarbon, a dehydroaromatized hydrocarbon, a dehydrocylized hydrocarbon, or a mixture thereof; (II) obtaining from the conversion effluent a first gaseous stream rich in the one or more upgraded hydrocarbons and the molecular hydrogen and a first particle stream rich in the coked catalyst particles; (III) contacting at least a portion of the coked catalyst particles in the first particle stream with an oxidant in a combustion zone to effect combustion of at least a portion of the coke to produce a combustion effluent comprising regenerated catalyst particles lean in coke and a combustion gas; (IV) obtaining from the combustion effluent a second gaseous stream rich in the combustion gas and a second particle stream rich in the regenerated catalyst particles; and (V) contacting an additional quantity of the hydrocarbon-containing feed with fluidized regenerated catalyst particles to produce additional conversion effluent comprising re-coked catalyst particles, additional one or more upgraded hydrocarbons, and additional molecular hydrogen, wherein a cycle time from the contacting the hydrocarbon-containing feed with the catalyst particles in step (I) to the contacting the additional quantity of the hydrocarbon-containing feed with the fluidized regenerated and reduced catalyst particles in step (V) is ≤60 minutes.

E2. The process of E1, further comprising, after step (IV) and before step (V), the following step: (IVa) contacting at least a portion of the regenerated catalyst particles with a reducing gas for a time period in a range from 1 second to less than 30 minutes to produce regenerated and reduced catalyst particles, wherein the additional quantity of the hydrocarbon-containing feed is contacted with fluidized regenerated and reduced catalyst particles in step (V).

E3. The process of E2, wherein at least a portion of the Group 8-10 element in the regenerated catalyst particles is at a higher oxidized state as compared to the Group 8-10 element in the catalyst particles contacted with the hydrocarbon-containing feed, and wherein at a least a portion of the Group 8-10 element in the regenerated and reduced catalyst particles is reduced to a lower oxidation state as compared to the Group 8-10 element in the regenerated catalyst particles.

E4. The process of E2 or E3, wherein in step (IVa), the regenerated catalyst particles and reducing gas are contacted at a temperature in a range from 450° C. to 900° C., preferably 600° C. to 900° C., more preferably 620° C. to 900° C., more preferably 650° C. to 850° C., or more preferably from 670° C. to 800° C.

E5. The process of any of E2 to 4, wherein in step (IVa), the regenerated catalyst particles and reducing gas are contacted under a reducing gas partial pressure in a range from 20 kPa-absolute to 1,000 kPa-absolute, preferably from 50 kPa-absolute to 500 kPa-absolute, or more preferably from 70 kPa-absolute to 300 kPa-absolute.

E6. The process of any of E2 to E5, wherein at least a portion of the Group 8-10 element in the regenerated and reduced catalyst particles is in the elemental state.

E7. The process of any of E2 to E6, wherein the reducing gas comprises molecular hydrogen, carbon monoxide, methane, ethane, ethylene, propane, propylene, steam, molecular nitrogen, argon, carbon dioxide, or a mixture thereof.

E8. The process of any of E2 to E7, wherein a cycle time from the contacting the hydrocarbon-containing feed with the catalyst particles in step (I) to the contacting the additional quantity of the hydrocarbon-containing feed with the fluidized regenerated and reduced catalyst particles in step (V) is ≤70 minutes, preferably from 1 minute to 70 minutes, or more preferably from 5 minutes to 45 minutes.

E9. The process of E1, wherein the cycle time is ≤55 minutes, ≤50 minutes, or ≤45 minutes.

E10. The process of any of E1 to E9, wherein in step (I), the hydrocarbon-containing feed and the catalyst particles are contacted with one another in the presence of steam at an amount in a range from 0.1 vol % to 50 vol %, preferably from 0.5 vol % to 30 vol %, or more preferably from 1 vol % to 15 vol %, based on a total volume of any $C_2$-$C_{16}$ alkanes and any $C_8$-$C_{16}$ alkyl aromatic hydrocarbons in the hydrocarbon-containing feed.

E11. The process of any of E1 to E9, wherein the support comprises the Group 2 element, and wherein in step (I), the hydrocarbon-containing feed and the catalyst particles are contacted with one another in the presence of steam at an amount in a range from 0.1 vol % to 50 vol %, preferably from 0.5 vol % to 30 vol %, or more preferably from 1 vol % to 15 vol %, based on a total volume of any $C_2$-$C_{16}$ alkanes and any $C_8$-$C_{16}$ alkyl aromatic hydrocarbons in the hydrocarbon-containing feed.

E12. The process of any of E1 to E9, wherein the support comprises the Group 4 element, and wherein in step (I), the hydrocarbon-containing feed and the catalyst particles are contacted with one another in the presence of steam at an amount in a range from 0.1 vol % to 50 vol %, preferably from 0.5 vol % to 30 vol %, or more preferably from 1 vol % to 15 vol %, based on a total volume of any $C_2$-$C_{16}$ alkanes and any $C_8$-$C_{16}$ alkyl aromatic hydrocarbons in the hydrocarbon-containing feed.

E13. The process of any of E1 to E9, wherein the support comprises the Group 12 element, and wherein in step (I), the hydrocarbon-containing feed and the catalyst particles are contacted with one another in the presence of steam at an amount in a range from 0.1 vol % to 50 vol %, preferably from 0.5 vol % to 30 vol %, or more preferably from 1 vol % to 15 vol %, based on a total volume of any $C_2$-$C_{16}$ alkanes and any $C_8$-$C_{16}$ alkyl aromatic hydrocarbons in the hydrocarbon-containing feed.

E14. The process of any of E1 to E9, wherein the support comprises the element having an atomic number of 21, 39, or 57-71, and wherein in step (I), the hydrocarbon-containing feed and the catalyst particles are contacted with one another in the presence of steam at an amount in a range from 0.1 vol % to 50 vol %, preferably from 0.5 vol % to 30 vol %, or more preferably from 1 vol % to 15 vol %, based on a total volume of any $C_2$-$C_{16}$ alkanes and any $C_8$-$C_{16}$ alkyl aromatic hydrocarbons in the hydrocarbon-containing feed.

E15. The process of any of E1 to E9, wherein the hydrocarbon-containing feed and the catalyst particles are contacted with one another in the absence of any steam or in the presence of less than 0.1 vol % of steam based on a total volume of any $C_2$-$C_{16}$ alkanes and any $C_8$-$C_{16}$ alkyl aromatic hydrocarbons in the hydrocarbon-containing feed.

E16. The process of any of E1 to E15, wherein the coked catalyst particles comprise agglomerations of the Group 8-10 element disposed on the support, and wherein at least a portion of the agglomerated Group 8-10 element disposed on the support is re-dispersed about the support during combustion of the coke in step (III).

E17. The process of any of E1 to E16, wherein the hydrocarbon-containing feed comprises propane, wherein the upgraded hydrocarbon comprises propylene, and wherein contacting the hydrocarbon-containing feed with the catalyst particles in step (I) has a propylene yield of at least 48%, at least 52%, or at least 62%, or at least 72% at a propylene selectivity of ≥75%, ≥80%, ≥85%, ≥90%, or ≥95%.

E18. The process of any of E1 to E17, wherein the hydrocarbon-containing feed comprises ≥70 vol % of propane, based on a total volume of the hydrocarbon-containing feed, wherein the hydrocarbon-containing feed and catalyst particles are contacted under a propane partial pressure of at least 40 kPa-absolute, and wherein contacting the hydrocarbon-containing feed with the catalyst particles in step (I) has a propylene yield of at least 48%, at least 52%, or at least 62%, or at least 72% at a propylene selectivity of ≥75%, ≥80%, ≥85%, ≥90%, or ≥95%.

E19. The process of any of E1 or E9 to E18, wherein steps (I) to (V) are repeated for at least 15 cycles, wherein the catalyst particles produce a first yield when initially contacted with the hydrocarbon-containing feed, and wherein the regenerated catalyst particles produce a second yield upon completion of the fifteenth cycle that is at least 98% of the first yield.

E20. The process of any of E2 to E18, wherein steps (I) to (V) are repeated for at least 15 cycles, wherein the catalyst particles produce a first yield when initially contacted with the hydrocarbon-containing feed, and wherein the regenerated and reduced catalyst particles produce a second yield upon completion of the fifteenth cycle that is at least 98% of the first yield.

E21. The process of any of E1 to E20, wherein the hydrocarbon-containing feed further comprises an inert gas comprising argon, neon, helium, molecular nitrogen, methane, or a mixture thereof.

E22. The process of any of E1 to E21, wherein in step (I), the hydrocarbon-containing feed and the catalyst particles are contacted at a temperature in a range from 600° C. to 900° C., preferably from 600° C. to 800° C., more preferably from 650° C. to 750° C., or more preferably from 670° C. to 720° C.

E23. The process of any of E1 to E22, wherein in step (I), the hydrocarbon-containing feed and the catalyst particles are contacted under a hydrocarbon partial pressure in a range from 20 kPa-absolute to 1,000 kPa-absolute, preferably from 50 kPa-absolute to 500 kPa-absolute, or more preferably 70 kPa-absolute to 300 kPa-absolute.

E24. The process of any of E1 to E23, wherein in step (III), the coked catalyst particles and oxidant are contacted at a temperature in a range from 600° C. to 1,100° C., preferably from 650° C. to 1,000° C., more preferably from 700° C. to 900° C., or more preferably from 750° C. to 850° C.

E25. The process of any of E1 to E24, wherein in step (III), the coked catalyst particles and oxidant are contacted under an oxidant partial pressure in a range from 20 kPa-absolute to 1,000 kPa-absolute, preferably from 50 kPa-absolute to 500 kPa-absolute, or more preferably from 100 kPa-absolute to 300 kPa-absolute.

E26. The process of any of E1 to E25, wherein the catalyst particles further comprise a promoter.

E27. The process of E26, wherein the promoter comprises Sn, Ga, Zn, Ge, In, Re, Ag, Au, Cu, a combination thereof, or a mixture thereof.

E28. The process of E26 or E27, wherein the promoter is disposed on the support.

E29. The process of any of E26 to E28, wherein the promoter is associated with the Group 8-10 element.

E30. The process of any of E26 to E29, wherein the promoter and the Group 8-10 element form Group 8-10 element-promoter clusters that are dispersed on the support.

E31. The process of any of E26 to E30, wherein the catalyst particles comprise up to 10 wt % of the promoter based on the total weight of the support.

E32. The process of any of E1 to E31, wherein the catalyst particles further comprise an alkali metal element disposed on the support.

E33. The process of E32, wherein the alkali metal element comprises Li, Na, K, Rb, Cs, a combination thereof, or a mixture thereof.

E34. The process of E32 or E33, wherein the catalyst particles comprise up to 5 wt % of the alkali metal element based on the total weight of the support.

E35. The process of any of E1 to E34, wherein the support comprises one or more of the following: $Mg_uZn_{1-u}O$, where u is a positive number; $Zn_vAl2O3_{+v}$, where v is a positive number; $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number; BeO; MgO; CaO; BaO; SrO; $BeCO_3$; $MgCO_3$; $CaCO_3$; $SrCO_3$, $BaCO_3$; $ZrO_2$; ZrC; ZrN; $ZrSiO_4$; $CaZrO_3$; $Ca_7ZrAl_6O_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)_2$; $Zn(ClO_3)_2$; $ZnSO_4$; $B_2O_6Zn_3$; $Zn_3N_2$; $ZnCO_3$; $CeO_2$; $Y_2O_3$; $La_2O_3$; $Sc_2O_3$; $Pr_6O_{11}$; $CePO_4$; $CeZrO_4$; $CeAlO_3$; $BaCeO_3$; $CePO_4$; Yttria-stabilized $ZrO_2$; combinations thereof, and mixtures thereof.

E36. The process of any of E1 to E35, wherein the support further comprises one or more of the following: $B_2O_3$; $Al_2O_3$; $SiO_2$; SiC; $Si_3N_4$; an aluminosilicate; VO; $V_2O_3$; $VO_2$; $V_2O_5$; $Ga_2O_3$; $In_2O_3$; $Mn_2O_3$; $Mn_3O_4$; MnO; a zeolite; combinations thereof; and mixture thereof.

E37. The process of any of E1 to E36, wherein the support is in the form of a plurality of primary particles comprising the Group 8-10 element disposed thereon.

E38. The process of any of E1 to E37, wherein the catalyst particles comprise primary particles having an average cross-sectional length in a range from 0.2 nm to 500 μm, preferably from 0.5 nm to 300 μm, more preferably from 1 nm to 200 μm, more preferably from 5 nm to 100 μm, and still more preferably from 2 nm to 100 nm, as measured by a transmission electron microscope.

E39. The process of any of E1 to E38, wherein the Group 8-10 element is disposed on the support such that the Group 8-10 element is the active component of the catalyst particles that effects the one or more of dehydrogenation, dehydroaromatization, and dehydrocyclization in step (I).

E40. The process of any of E1 to E39, wherein the support has a surface area in a range from 0.1 m²/g to 1,500 m²/g, preferably from 1 m²/g to 1,000 m²/g, more preferably from 10 m²/g to 800 m²/g, or more preferably from 100 m²/g to 500 m²/g.

E41. The process of any of E1 to E40, wherein the hydrocarbon-containing feed and catalyst particles are contacted in step (I) for a time period in a range from 0.1 seconds to 1.5 minutes, preferably from of 0.5 seconds to 1 minute, or more preferably from 1 seconds to 30 seconds.

E42. The process of any of E1 to E41, wherein a weight ratio of the catalyst particles to a combined amount of any $C_2$-$C_{16}$ alkanes and any $C_8$-$C_{16}$ aromatic hydrocarbons is in a range from 1 to 150, preferably from 5 to 100, or more preferably from 10 to 80.

E43. The process of any of E1 to E42, wherein the hydrocarbon-containing feed contacts the catalyst in step (I) at a weight hourly space velocity in a range from 0.1 hr$^{-1}$ to 100 hr$^{-1}$, preferably from 0.2 hr$^{-1}$ to 64 hr$^{-1}$, or more preferably from 0.4 hr$^{-1}$ to 32 hr$^{-1}$, based on the weight of any $C_2$-$C_{16}$ alkanes and any $C_8$-$C_{16}$ aromatic hydrocarbons in the hydrocarbon-containing feed.

E44. The process of any of E1 to E43, wherein the hydrocarbon-containing feed comprises ethane, propane, isobutane, butane, ethylbenzene, propylbenzene, methylethylbenzene, or a mixture thereof.

E45. The process of any of E1 to E44, further comprising contacting a supplemental fuel with the oxidant in the combustion zone in step (III) to effect combustion of at least a portion of the supplemental fuel to produce heat and an additional quantity of combustion gas.

E46. The process of E45, wherein the supplemental fuel comprises molecular hydrogen, methane, ethane, propane, or a mixture thereof.

E47. The process of any of E1 to E46, wherein the catalyst particles are in the form of a dense turbulent fluidized bed when contacted with the hydrocarbon-containing feed.

E48. The process of any of E1 to E46, wherein the conversion zone is disposed within a riser reactor.

E49. The process of any of E1 to E46, wherein the conversion zone is disposed within a downer reactor.

E50. The process of any of E1 to E49, wherein the hydrocarbon-containing feed and the catalyst particles are in concurrent flow, counter-current flow, or a combination thereof when contacted with one another.

E51. The process of any of E1 to E50, wherein a first portion of the coked catalyst particles in first particle stream rich in the coked catalyst particles is contacted with the oxidant in the combustion zone in step (II), and wherein a second portion of the coked catalyst particles in the first particle stream rich in the coked catalyst particles is contacted with the additional quantity of the hydrocarbon-containing feed in step (V).

E52. The process of any of E2 to E51, wherein a first portion of the coked catalyst particles in first particle stream rich in the coked catalyst particles is contacted with the oxidant in the combustion zone in step (II), and wherein a second portion of the coked catalyst particles in the first particle stream rich in the coked catalyst particles is contacted with the reducing gas in step (IVa).

E53. The process of any of E2 to E51, wherein a first portion of the coked catalyst particles in first particle stream rich in the coked catalyst particles is contacted with the oxidant in the combustion zone in step (II), wherein a second portion of the coked catalyst particles in the first particle stream rich in the coked catalyst particles is contacted with the reducing gas in step (IVa), and wherein a third portion of the coked catalyst particles in the first particle stream rich in the coked catalyst particles is contacted with the additional quantity of the hydrocarbon-containing feed in step (V).

E54. The process of any of E1 to E53, further comprising: removing a portion of the catalyst particles from the conversion zone during contact of the hydrocarbon-containing feed with the fluidized catalyst particles during step (I); heating the portion of the catalyst particles removed from the conversion zone to produce heated catalyst particles; and feeding the heated catalyst particles into the conversion zone to contact the hydrocarbon-containing feed.

E55. The process of any of E1 to E54, further comprising supplying heat to the catalyst particles within the conversion zone during contact of the catalyst particles with the hydrocarbon-containing feed.

E56. The process of any of E1 to E55, wherein the catalyst particles have a particle density in a range from 0.5 g/cm³ to 3 g/cm³, 0.7 g/cm³ to 2 g/cm³, or 0.8 g/cm³ to 1.4 g/cm³.

E57. The process of any of E1 to E55, wherein the catalyst particles have a size and particle density that are consistent with a Geldart A definition.

E58. The process of any of E1 to E57, wherein the support comprises ≥3 wt %, ≥6 wt %, ≥11 wt %, ≥15 wt %, or ≥20 wt % of a Group 2 element.

E59. The process of E58, wherein the Group 2 element comprises Mg.

E60. The process of any of E1 to E59, wherein the support comprises calcined hydrotalcite.

E61. The process of any of E2 to E60, wherein, in step (IVa), the temperature range is from 620° C. to 900° C. and the time period is from 1 second to 10 minutes or 1 second to 5 minutes to produce the regenerated and reduced catalyst particles.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for upgrading a hydrocarbon, comprising:
   (I) contacting a hydrocarbon-containing feed with fluidized catalyst particles comprising a Group 8-10 element disposed on a support within a conversion zone to effect one or more of dehydrogenation, dehydroaromatization, and dehydrocyclization of at least a portion of the hydrocarbon-containing feed to produce a conversion effluent comprising fluidized coked catalyst particles, one or more upgraded hydrocarbons, and molecular hydrogen, wherein:
   the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof;
   the hydrocarbon-containing feed and fluidized catalyst particles are contacted at a temperature in a range from 300° C. to 900° C., for a time period in a range from 0.1 seconds to 2 minutes, under a hydrocarbon partial pressure of at least 20 kPa-absolute, wherein the hydrocarbon partial pressure is the total partial pressure of any $C_2$-$C_{16}$ linear or branched alkanes, any $C_4$-$C_{16}$ cyclic alkanes, and any $C_8$-$C_{16}$ alkyl aromatic hydrocarbons in the hydrocarbon-containing feed;

the hydrocarbon-containing feed and the fluidized catalyst particles are contacted with one another in a presence of steam at an amount in a range from 0.1 vol % to 50 vol %, based on a total volume of any $C_2$-$C_{16}$ linear or branched alkanes, any $C_4$-$C_{16}$ cyclic alkanes, and any $C_8$-$C_{16}$ alkyl aromatic hydrocarbons in the hydrocarbon-containing feed;

the fluidized catalyst particles comprise from 0.001 wt % to 6 wt % of the Group 8-10 element based on the weight of the support; and the one or more upgraded hydrocarbons comprise a dehydrogenated hydrocarbon, a dehydroaromatized hydrocarbon, a dehydrocylized hydrocarbon, or a mixture thereof;

(II) obtaining from the conversion effluent a first gaseous stream rich in the one or more upgraded hydrocarbons and the molecular hydrogen and a first particle stream rich in the fluidized coked catalyst particles;

(III) contacting at least a portion of the fluidized coked catalyst particles in the first particle stream with an oxidant in a combustion zone to effect combustion of at least a portion of the coke to produce a combustion effluent comprising fluidized regenerated catalyst particles lean in coke and a combustion gas;

(IV) obtaining from the combustion effluent a second gaseous stream rich in the combustion gas and a second particle stream rich in the fluidized regenerated catalyst particles;

(IVa) contacting at least a portion of the fluidized regenerated catalyst particles with a reducing gas for a time period in a range from 1 second to less than 30 minutes to produce fluidized regenerated and reduced catalyst particles; and (V) contacting an additional quantity of the hydrocarbon-containing feed with the fluidized regenerated and reduced catalyst particles to produce additional conversion effluent comprising fluidized re-coked catalyst particles, additional one or more upgraded hydrocarbons, and additional molecular hydrogen, wherein a cycle time from the contacting the hydrocarbon-containing feed with the fluidized catalyst particles in step (I) to the contacting the additional quantity of the hydrocarbon-containing feed with the fluidized regenerated and reduced catalyst particles in step (V) is ≤60 minutes.

2. The process of claim 1, wherein, in step (IVa), the fluidized regenerated catalyst particles and reducing gas are contacted at a temperature in a range from 700° C. to 900° C.

3. The process of claim 1, wherein the cycle time is in an range from 1 minute to 45 minutes.

4. The process of claim 1, wherein the support comprises a mixed Mg/Al metal oxide, and wherein in step (I), the hydrocarbon-containing feed and the fluidized catalyst particles are contacted with one another in the presence of steam at an amount in a range from 0.1 vol % to 30 vol %, based on a total volume of any $C_2$-$C_{16}$ alkanes and any $C_8$-$C_{16}$ alkyl aromatic hydrocarbons in the hydrocarbon-containing feed.

5. The process of claim 1, wherein the support comprises a mixed Mg/Al metal oxide, and wherein in step (I), the hydrocarbon-containing feed and the fluidized catalyst particles are contacted with one another in the presence of steam at an amount in a range from 0.1 vol % to 15 vol %, based on a total volume of any $C_2$-$C_{16}$ linear or branched alkanes, any $C_4$-$C_{16}$ cyclic alkanes, and any $C_8$-$C_{16}$ alkyl aromatic hydrocarbons in the hydrocarbon-containing feed.

6. The process of claim 1, wherein the hydrocarbon-containing feed comprises ≥80 vol % of propane, based on a total volume of the hydrocarbon-containing feed, wherein the hydrocarbon-containing feed and the fluidized catalyst particles are contacted under a propane partial pressure of at least 100 kPa-absolute, and wherein contacting the hydrocarbon-containing feed with the fluidized catalyst particles in step (I) has a propylene yield of at least 48% at a propylene selectivity of ≥75%.

7. The process of claim 1, wherein in step (I), at least one of the following is met:
(i) the hydrocarbon-containing feed and the fluidized catalyst particles are contacted at a temperature in a range from 550° C. to 900° C.; and
(ii) the hydrocarbon-containing feed and the fluidized catalyst particles are contacted under a hydrocarbon partial pressure in a range from 20 kPa-absolute to 1,000 kPa-absolute.

8. The process of claim 1, wherein in step (III), the fluidized coked catalyst particles and oxidant are contacted at a temperature in a range from 700° C. to 1,100° C.

9. The process of claim 1, wherein the fluidized catalyst particles further comprise a promoter, and wherein the promoter comprises Sn, Ga, Zn, Ge, In, Re, Ag, Au, Cu, a combination thereof, or a mixture thereof.

10. The process of claim 1, wherein the fluidized catalyst particles further comprise an alkali metal element selected from Li, Na, K, Rb, Cs, and combinations and mixtures thereof disposed on the support, and wherein the fluidized catalyst particles comprise up to 5 wt % of the alkali metal element based on the weight of the support.

11. The process of claim 1, wherein the fluidized catalyst particles are in the form of a dense turbulent fluidized bed when contacted with the hydrocarbon-containing feed.

12. The process of claim 1, wherein the conversion zone is disposed within a riser reactor or a down reactor.

13. The process of claim 1, wherein a first portion of the fluidized coked catalyst particles in the first particle stream rich in the fluidized coked catalyst particles is contacted with the oxidant in the combustion zone in step (II), and wherein a second portion of the fluidized coked catalyst particles in the first particle stream rich in the fluidized coked catalyst particles is contacted with the additional quantity of the hydrocarbon-containing feed in step (V).

14. The process of claim 1, further comprising:
removing a portion of the fluidized catalyst particles from the conversion zone during contact of the hydrocarbon-containing feed with the fluidized catalyst particles during step (I);
heating the portion of the fluidized catalyst particles removed from the conversion zone to produce heated fluidized catalyst particles, wherein the portion of the fluidized catalyst particles is heated by (i) indirectly transferring heat from a heat transfer medium or (ii) an electric heater; and
feeding the heated fluidized catalyst particles into the conversion zone to contact the hydrocarbon-containing feed.

15. The process of claim 1, further comprising supplying heat to the fluidized catalyst particles within the conversion zone during contact of the fluidized catalyst particles with the hydrocarbon-containing feed.

16. The process of claim 1, wherein the fluidized catalyst particles have a size and particle density that are consistent with a Geldart A definition.

17. The process of claim 1, wherein, in step (IVa), the temperature range is from 700° C. to 900° C. and the time period is <1 minute to produce the fluidized regenerated and reduced catalyst particles.

18. The process of claim 1, wherein:
the support comprises ≥3 wt % of one or more Group 2 elements;
in step (IVa), the temperature range is from ≥720° C. to 900° C. and the time period is <1 minute to produce the fluidized regenerated and reduced catalyst particles; and
in step (V), the cycle time is ≤45 minutes.

19. The process of claim 1, wherein:
the support comprises a mixed Mg/Al metal oxide;
in step (IVa), the temperature range is from >700° C. to 900° C. and the time period is <1 minute to produce the fluidized regenerated and reduced catalyst particles; and
in step (V), the cycle time is ≤45 minutes.

20. The process of claim 1, wherein:
the support comprises calcined hydrotalcite;
in step (IVa), the temperature range is from >700° C. to 900° C. and the time period is <1 minute to produce the fluidized regenerated and reduced catalyst particles; and
in step (V), the cycle time is ≤45 minutes.

21. The process of claim 1, wherein:
the fluidized catalyst particles comprise <0.025 wt % of the Group 8-10 element based on the weight of the support;
the Group 8-10 element comprises Pt; and
the support comprises a mixed Mg/Al metal oxide.

22. The process of claim 1, wherein the support comprises a mixed Mg/Al metal oxide, and wherein in step (I), the hydrocarbon-containing feed and the fluidized catalyst particles are contacted with one another in the presence of steam at an amount in a range from 0.1 vol % to 10 vol %, based on a total volume of any $C_2$-$C_{16}$ linear or branched alkanes, any $C_4$-$C_{16}$ cyclic alkanes, and any $C_8$-$C_{16}$ alkyl aromatic hydrocarbons in the hydrocarbon-containing feed.

23. The process of claim 1, wherein the support comprises a mixed Mg/Al metal oxide, and wherein in step (I), the hydrocarbon-containing feed and the fluidized catalyst particles are contacted with one another in the presence of steam at an amount in a range from 0.1 vol % to 5 vol %, based on a total volume of any $C_2$-$C_{16}$ linear or branched alkanes, any $C_4$-$C_{16}$ cyclic alkanes, and any $C_8$-$C_{16}$ alkyl aromatic hydrocarbons in the hydrocarbon-containing feed.

24. The process of claim 1, wherein:
the catalyst further comprises up to 10 wt % of a promoter disposed on the support based on the weight of the support;
the promoter comprises Sn;
the Group 8-10 element comprises Pt;
the support comprises a mixed Mg/Al metal oxide;
in step (I), the hydrocarbon-containing feed and the fluidized catalyst particles are contacted with one another in the presence of steam at an amount in a range from 0.5 vol % to 20 vol %, based on a total volume of any $C_2$-$C_{16}$ linear or branched alkanes, any $C_4$-$C_{16}$ cyclic alkanes, and any $C_8$-$C_{16}$ alkyl aromatic hydrocarbons in the hydrocarbon-containing feed;
in step (III), the fluidized coked catalyst particles and oxidant are contacted at a temperature in a range from >700° C. to 1,100° C.;
in step (IVa), the fluidized regenerated catalyst particles are contacted with the reducing gas at a temperature in a range from >700° C. to 900° C. and the time period is <1 minute to produce the fluidized regenerated and reduced catalyst particles; and
in step (V), the cycle time is ≤20 minutes.

25. The process of claim 1, wherein:
the catalyst further comprises up to 10 wt % of a promoter disposed on the support based on the weight of the support;
the promoter comprises Sn;
the Group 8-10 element comprises Pt;
the support comprises a mixed Mg/Al metal oxide;
in step (I), the hydrocarbon-containing feed and the fluidized catalyst particles are contacted with one another in the presence of steam at an amount in a range from 0.5 vol % to 20 vol %, based on a total volume of any $C_2$-$C_{16}$ linear or branched alkanes, any $C_4$-$C_{16}$ cyclic alkanes, and any $C_8$-$C_{16}$ alkyl aromatic hydrocarbons in the hydrocarbon-containing feed;
in step (III), the fluidized coked catalyst particles and oxidant are contacted at a temperature in a range from ≥750° C. to 1,100° C.;
in step (IVa), the fluidized regenerated catalyst particles are contacted with the reducing gas at a temperature in a range from ≥720° C. to 900° C. and the time period is <30 seconds to produce the fluidized regenerated and reduced catalyst particles; and
in step (V), the cycle time is ≤20 minutes.

* * * * *